(12) United States Patent
Auge, II et al.

(10) Patent No.: US 7,771,422 B2
(45) Date of Patent: *Aug. 10, 2010

(54) METHODS AND DEVICES FOR ELECTROSURGERY

(75) Inventors: Wayne K. Auge, II, Santa Fe, NM (US); Roy E. Morgan, San Jose, CA (US)

(73) Assignee: NuOrtho Surgical, Inc., Fall River, MA (US)

( * ) Notice: Subject to any disclaimer, the term of this patent is extended or adjusted under 35 U.S.C. 154(b) by 1618 days.

This patent is subject to a terminal disclaimer.

(21) Appl. No.: 11/006,079

(22) Filed: Dec. 6, 2004

(65) Prior Publication Data

US 2005/0085806 A1    Apr. 21, 2005

Related U.S. Application Data

(63) Continuation-in-part of application No. PCT/US03/18116, filed on Jun. 6, 2003.

(60) Provisional application No. 60/387,114, filed on Jun. 6, 2002, provisional application No. 60/387,775, filed on Jun. 10, 2002.

(51) Int. Cl.
*A61B 18/14* (2006.01)

(52) U.S. Cl. .............................. 606/41; 606/45; 606/49

(58) Field of Classification Search ................... 606/32, 606/41
See application file for complete search history.

(56) References Cited

U.S. PATENT DOCUMENTS

| | | |
|---|---|---|
| 3,911,107 A | 10/1975 | Krezanoski |
| 3,941,135 A | 3/1976 | von Sturm et al. |
| 3,982,017 A | 9/1976 | Thiele |
| 4,014,777 A | 3/1977 | Brown |
| 4,105,017 A | 8/1978 | Ryaby et al. |
| 4,266,532 A | 5/1981 | Ryaby et al. |
| 4,266,533 A | 5/1981 | Ryaby et al. |
| 4,504,493 A | 3/1985 | Marshall et al. |
| 4,540,409 A | 9/1985 | Nystrom et al. |

(Continued)

FOREIGN PATENT DOCUMENTS

GB        2037920        7/1980

(Continued)

OTHER PUBLICATIONS

Babincova, Melina et al., ""High-Gradient Magnetic Capture of Ferrofluids: Implications for Drug Targeting and Tumor Embolization"", *Zeitschrift fur Naturforschung*, vol. 56-C 2001, 909-911.

(Continued)

*Primary Examiner*—Lee S Cohen
(74) *Attorney, Agent, or Firm*—Janeen Vilven; Vidal Z. Oaxaca; Peacock Myers, P.C.

(57) ABSTRACT

Devices and methods for electrolytic electrosurgery wherein a detector is located proximal to an active electrode on an electrosurgical probe, optionally disposed between the active electrode and a return electrode, the detector detecting at least on parameter relating to electrolysis. The detected parameter can include pH concentration, temperature, conductivity, impedance, ion, concentration, electrolytic gas consumption, electrolytic gas production, pressure or sound. The detected parameter can be employed in control systems to control systems to control activation or operation of the electrosurgical probe.

7 Claims, 11 Drawing Sheets

U.S. PATENT DOCUMENTS

| | | | |
|---|---|---|---|
| 4,615,347 A | 10/1986 | Schooley | |
| 4,872,865 A | 10/1989 | Bloebaum et al. | |
| 4,938,970 A | 7/1990 | Hustead et al. | |
| 4,971,068 A * | 11/1990 | Sahi | 600/576 |
| 5,014,699 A | 5/1991 | Pollack et al. | |
| 5,236,456 A | 8/1993 | O'Leary et al. | |
| 5,282,861 A | 2/1994 | Kaplan | |
| 5,304,724 A | 4/1994 | Newton | |
| 5,314,476 A | 5/1994 | Prewett et al. | |
| 5,352,463 A | 10/1994 | Badylak et al. | |
| 5,360,440 A | 11/1994 | Andersen | |
| 5,366,443 A | 11/1994 | Eggers et al. | |
| 5,403,825 A | 4/1995 | Lagarde et al. | |
| 5,458,596 A | 10/1995 | Lax et al. | |
| 5,494,538 A | 2/1996 | Kirillov et al. | |
| 5,498,259 A | 3/1996 | Mourant et al. | |
| 5,514,130 A * | 5/1996 | Baker | 606/41 |
| 5,516,533 A | 5/1996 | Badylak et al. | |
| 5,554,141 A | 9/1996 | Wendler | |
| 5,569,242 A * | 10/1996 | Lax et al. | 606/42 |
| 5,584,863 A | 12/1996 | Rauch et al. | |
| 5,622,725 A | 4/1997 | Kross | |
| 5,669,904 A | 9/1997 | Platt et al. | |
| 5,669,907 A | 9/1997 | Platt et al. | |
| 5,669,934 A | 9/1997 | Sawyer | |
| 5,683,366 A | 11/1997 | Eggers et al. | |
| 5,697,281 A | 12/1997 | Eggers et al. | |
| 5,697,536 A * | 12/1997 | Eggers et al. | 604/114 |
| 5,697,882 A | 12/1997 | Eggers et al. | |
| 5,697,909 A | 12/1997 | Eggers et al. | |
| 5,741,261 A | 4/1998 | Moskovitz et al. | |
| 5,746,896 A | 5/1998 | Shimamune et al. | |
| 5,749,895 A | 5/1998 | Sawyer et al. | |
| 5,788,976 A | 8/1998 | Bradford | |
| 5,800,385 A | 9/1998 | Demopulos et al. | |
| 5,820,583 A | 10/1998 | Demopulos et al. | |
| 5,824,015 A | 10/1998 | Sawyer | |
| 5,840,166 A | 11/1998 | Kaneko | |
| 5,855,608 A | 1/1999 | Brekke | |
| 5,860,950 A | 1/1999 | Demopulos et al. | |
| 5,871,469 A | 2/1999 | Eggers et al. | |
| 5,885,292 A | 3/1999 | Moskovitz et al. | |
| 5,919,191 A | 7/1999 | Lennox et al. | |
| 5,955,514 A | 9/1999 | Huang et al. | |
| 5,964,968 A | 10/1999 | Kaneko | |
| 6,032,077 A | 2/2000 | Pomeranz | |
| 6,033,654 A | 3/2000 | Stedronsky et al. | |
| 6,086,585 A | 7/2000 | Hovda et al. | |
| 6,112,122 A | 8/2000 | Schwardt et al. | |
| 6,117,109 A | 9/2000 | Eggers et al. | |
| 6,135,998 A | 10/2000 | Palanker | |
| 6,149,620 A | 11/2000 | Baker et al. | |
| 6,159,194 A | 12/2000 | Eggers et al. | |
| 6,162,219 A | 12/2000 | Nilsson et al. | |
| 6,174,309 B1 * | 1/2001 | Wrublewski et al. | 606/45 |
| 6,206,878 B1 | 3/2001 | Bishop et al. | |
| 6,213,999 B1 | 4/2001 | Platt et al. | |
| 6,214,003 B1 | 4/2001 | Morgan et al. | |
| 6,224,592 B1 | 5/2001 | Eggers et al. | |
| 6,235,024 B1 | 5/2001 | Tu | |
| 6,241,723 B1 | 6/2001 | Heim et al. | |
| 6,241,753 B1 | 6/2001 | Knowlton | |
| 6,264,650 B1 * | 7/2001 | Hovda et al. | 606/32 |
| 6,264,652 B1 | 7/2001 | Eggers et al. | |
| 6,273,883 B1 | 8/2001 | Furumoto | |
| 6,293,942 B1 | 9/2001 | Goble et al. | |
| 6,306,134 B1 | 10/2001 | Goble et al. | |
| 6,309,387 B1 | 10/2001 | Eggers et al. | |
| 6,322,549 B1 | 11/2001 | Eggers et al. | |
| 6,350,276 B1 | 2/2002 | Knowlton | |
| 6,383,184 B1 * | 5/2002 | Sharkey | 606/41 |
| 6,391,025 B1 | 5/2002 | Weinstein et al. | |
| 6,416,509 B1 * | 7/2002 | Goble et al. | 606/37 |
| 6,419,815 B1 | 7/2002 | Chambers et al. | |
| 6,461,352 B2 | 10/2002 | Morgan et al. | |
| 6,463,336 B1 | 10/2002 | Mawhinney | |
| 6,471,993 B1 | 10/2002 | Shastri et al. | |
| 6,547,794 B2 | 4/2003 | Auge | |
| 6,558,382 B2 * | 5/2003 | Jahns et al. | 606/41 |
| 6,772,013 B1 | 8/2004 | Ingle et al. | |
| 6,780,178 B2 | 8/2004 | Palanker et al. | |
| 6,824,555 B1 | 11/2004 | Towler et al. | |
| 6,832,995 B1 | 12/2004 | Towler et al. | |
| 6,890,332 B2 | 5/2005 | Truckai et al. | |
| 6,902,564 B2 | 6/2005 | Morgan et al. | |
| 7,066,932 B1 | 6/2006 | Morgan et al. | |
| 7,105,011 B2 | 9/2006 | Auge | |
| 7,354,438 B2 | 4/2008 | Morgan et al. | |
| 7,445,619 B2 * | 11/2008 | Auge et al. | 606/41 |
| 7,549,989 B2 | 6/2009 | Morgan et al. | |
| 2001/0007940 A1 | 7/2001 | Tu et al. | |
| 2002/0165596 A1 | 11/2002 | Wilson | |
| 2003/0028189 A1 | 2/2003 | Woloszko et al. | |
| 2003/0216732 A1 * | 11/2003 | Truckai et al. | 606/49 |
| 2003/0216733 A1 * | 11/2003 | McClurken et al. | 606/51 |
| 2004/0167244 A1 | 8/2004 | Auge, II | |
| 2004/0267255 A1 | 12/2004 | Auge, II et al. | |
| 2005/0182449 A1 | 8/2005 | Auge, II et al. | |
| 2009/0030410 A1 | 1/2009 | Auge, II et al. | |
| 2009/0306645 A1 | 12/2009 | Morgan et al. | |

FOREIGN PATENT DOCUMENTS

| | | |
|---|---|---|
| WO | WO-02/102438 | 12/2002 |
| WO | WO-03/015865 | 2/2003 |
| WO | WO-03/103521 | 12/2003 |

OTHER PUBLICATIONS

Brennetot, R. et al., "Investigation of Chelate Formation, Intramoecular Energy Transfer and Luminescence Efficiency and Lifetimes in the Euthenoyltrifluoroacetone-trioctylphosphine oxide-Triton x-100 System Using Absorbance, Fluorescence and Photothermal Measurements", *Spectrochim ACTA A Mol. Biomol. Spectrosc.*, Part A-56 2000 , 702-715.

Edwards, R B. et al., "Thermometric determination of cartilage matrix temperatures during thermal chondroplasty: comparison of bipolar and monopolar radiofrequency devices", *Arthroscopy* Apr. 2002;18(4), 339-346.

Grant, Kyle M. et al., ""Magnetic Field-Controlled Microfluidic Transport"", *Journal of American Chemical Society (JACS) Articles*, vol. 124, No. 3 2002 , 462-467.

Medvecky, Michael J. et al., "Thermal Capsular Shrinkage: Basic Science and Clinical Applications", *Arthroscopy*, 2001, vol. 17, No. 6 Jul. 2001 , 624-635.

Minczykowski, Andrzej et al., ""Effects of Magnetic Resonance Imaging on Polymorphonuclear Neutrophil Adhesion"", *Diagnostics and Medical Technolgy, Medical Science Monitor*, vol. 7(3) 2001 , 482-488.

Torchilin, Vladimir P. et al., ""Drug Targeting"", *European Journal of Pharmaceutical Sciences*, vol. 11, Supplement 2 2000 , S81-S91.

Zhang, Min et al., ""Effects of the Demineralization Process on the Osteoinductivity of Demineralized Bone Matrix"", *J. Periodontaol*, vol. 68 No. 11 Nov. 1997 , 1085-1092.

Zohar, Ofer et al., ""Thermal Imaging of Reeptor-Activated Heat Production in Single Cells"", *Biophysical Journal*, vol. 74 Jan. 1998, 82-89.

Chen, S. S. et al., "Heat-Induced Changes in the Mechanics of a Collagenous Tissue: Isothermal, Isotonic Shrinkage", *Transactions of the ASME* vol. 120 1998, 382-388.

Fink, Bernd et al., "Holmium: YAG Laser-Induced Aseptic Bone Necroses of the Femoral Condyle", *Arthroscopy: The Journal of Arthroscopic and Related Surgery* vol. 12 No. 2 1996 , 217-223.

Gould, Stephen E. et al., "Cellular Contribution of Bone Graft to Fusion", *Journal of Orthopaedic Research* vol. 18 2000 , 920-927.

Ito, Takayasu et al., "Sensitivity of Osteoinductive Activity of Deminerlization and Defatted Rat Femur to Temperature and Duration of Heating", *Clinical Orthopaedics and Related Research* No. 316 1995, 267-275.

Janzen, Dennis L. et al., "Osteonecrosis After Contact Neodymium: Yttrium Aluminum Garnet Arthroscopic Laser Meniscectomy", *AJR 169* 1997, 855-858.

Lopez, Mandi J. et al., "Effects of Monopolar Radiofrequency Energy on Ovine Joint Capsular Mechanical Properties", *Clinical Orthopaedics and Related Research*, No. 374 2000, 286-297.

Mourant, Judith R. et al., "Improvements in Laser "Welding" of Chicken Bone Tibias in vitro", *Laser Sciences and Applications Group*, Los Alamos, NM, 1-8, 2000.

Mourant, Judith R. et al., "Laser Welding of Bone: Successful in vitro Experiments", *Laser Sciences and Applications Group*, Los Alamos, NM, 1-5, 2000.

Rozbruch, S. R. et al., "Osteonecrosis of the Knee Following Arthroscopic Laser Meniscectomy", *Arthroscopy: The Journal of Arthroscopic and Related Surgery* vol. 12 No. 2 1996, 245-250.

Thal, Raymond et al., "Delayed Articular Cartilage Slough: Two Cases Resulting From Holmium: YAG Laser Damage to Normal Articular Cartilage and a Review of the Literature", *Arthroscopy: The Journal of Arthroscopic and Related Surgery* vol. 12 No. 1 1996, 92-94.

Wall, Michael S. et al., "Thermal Modification of Collagen", *J. Shoulder Elbow Surg.* vol. 8 No. 4 1999, 339-344.

Wallace, Andrew L. et al., "Electrothermal Shrinkage Reduces Laxity but Alters Creep Behavior in a Lapine Ligament Model", *J. Shoulder Elbow Surg.* vol. 10 No. 1 2001, 1-6.

* cited by examiner

METHODS AND DEVICES FOR ELECTROSURGERY

CROSS-REFERENCE TO RELATED APPLICATIONS

This application is a continuation-in-part application of International Application No. PCT/US03/18116, International Publication No. WO 03/103521, entitled "Methods and Devices for Electrosurgery", filed on Jun. 6, 2003 and the specification thereof is incorporated herein by reference.

This application claims the benefit of the filing of U.S. Provisional Patent Application Ser. No. 60/387,114, entitled Methods and Devices for Electrosurgery, filed on Jun. 6, 2002, and of U.S. Provisional Patent Application Ser. No. 60/387,775, entitled Methods and Devices for Electrosurgical Electrolysis, filed on Jun. 10, 2002, and the specification of each of the foregoing is incorporated herein by reference.

The subject of this application is related to U.S. patent application Ser. No. 10/119,671, entitled Methods and Devices for Electrosurgery, to Morgan, et al., filed on Apr. 9, 2002, and to U.S. patent application Ser. No. 10/157,651, entitled Biologically Enhanced Irrigants, to Morgan, et al., filed on May 28, 2002 and the specifications thereof are incorporated herein by reference.

BACKGROUND OF THE INVENTION

1. Field of the Invention (Technical Field)

The present invention relates to methods and devices for electrosurgery, including devices that operate in an electrolyzable media, including an aqueous electrolyzable media, by means of electrolysis and oxy-hydrogen combustion, and such devices with sensors and detectors for electrolysis and oxy-hydrogen combustion-specific parameters.

2. Description of Related Art

Note that the following discussion refers to a number of publications by author(s) and year of publication, and that due to recent publication dates certain publications are not to be considered as prior art vis-à-vis the present invention. Discussion of such publications herein is given for more complete background and is not to be construed as an admission that such publications are prior art for patentability determination purposes.

Electrosurgical devices have become widely popular for use in many medical treatment settings. However, limits in the ability to detect and measure the relevant parameters of the electrosurgical process have been known to impair the practitioner's ability to accurately and contemporaneously alter the electrosurgical application procedure to guard against treatment sequelae, induced iatrogenic damage, or to hinder the attainment of attaining treatment goals.

Although the need for such detection and measuring devices has been recently recognized, prior art contemplation and/or development of such devices has been limited to electrosurgical bulk property measurements such as temperature, fluid field impedance, and fluid field capacitance. This limitation has been due to both the inherent constraints in developing sensing and measuring devices within the foundation of the physiochemical paradigm of electrosurgery disclosed in the prior art, and to the perceived importance of such bulk property measurement for determining the extent and effect of electrosurgery.

As disclosed in U.S. patent application Ser. No. 10/119,671, electrosurgery has been incorrectly construed as being governed by plasma formation or related forms of ionization (see, e.g., U.S. Pat. Nos. 5,669,904, 6,206,878, 6,213,999, 6,135,998, 5,683,366, 5,697,882, 6,149,620, 6,241,723, 6,264,652, 6,322,549, 6,306,134 and 6,293,942, and the like), and this misconception has led to limited contemplation and development of detection and measuring devices for use during electrosurgical therapeutic applications. For example, in the plasma physiochemical paradigm of electrosurgery, it would be anticipated that detection and measuring devices would be contemplated and/or developed that require the use of instruments that can detect and measure the high energy emissions of plasma formation. Such emissions would include radiation elements such as free electrons, alpha particles, gamma particles, and x-rays. This approach has not been implemented, despite claims in the prior art that sufficient radiation signal intensity by means of a plasma is generated by the electrosurgical process, relative to normal background levels of radiation noise, necessary for treatment protocols and therapeutic effects. If sufficient radiation signal intensity is demonstrated, it would follow that useful detection and measuring devices could be developed with sensing and measuring algorithms for correlating these radiation measurements to treatment effects. However, this endeavor would require multivariate response surface modeling. Because modeling correlates currently exist only for highly idealized plasma generating environments utilizing vacuum chambers and/or magnetic field control, such detection and measuring devices have not been pursued. Extrapolating such ideal conditions to the in vivo application of electrosurgery methods and devices would prove insurmountable. For this reason, no further development of sensing and measuring devices of the electrosurgical process have been developed other than that of bulk property measurements; thus, plasma-related electrosurgical physiochemical paradigms have constrained the conceptualization and development of sensing and measuring devices for electrosurgery to those of the bulk property measurements as disclosed in prior art.

The perceived importance of bulk property measurement for determining the extent and effect of electrosurgery has been well documented. Quantifying energy input indirectly through temperature measurement, fluid field impedance measurement, and fluid field capacitance measurement is believed to indicated the degree to which electrosurgery will effect tissue and the host response thereof. Since such correlations have been extremely inconsistent in practice, a significant amount of confusion has surfaced regarding therapeutic electrosurgical protocols, often leading to the reduction in use of electrosurgical devices for certain applications. See, e.g., Thermometric determination of cartilage matrix temperatures during thermal chondroplasty: comparison of bipolar and monopolar radiofrequency devices. *Arthroscopy*, 2002 April; 18(4):339-46. The reliance upon bulk property measurements in developing therapeutic protocols incompletely addresses the true physiochemical processes of electrosurgery based upon the more detailed understanding of electrosurgery processes and phenomena described herein.

In the prior art, for example, temperature sensing devices have been disclosed that allow feedback measurement of the treatment environment temperature, such as referenced in U.S. Pat. Nos. 6,162,217, 5,122,137 and U.S. Published Patent Application 2001/0029369, and the like. These methods have been determined to be inaccurate due to the typically rapid changing milieu of the treatment locale. See, e.g., Radiofrequency energy-induced heating of bovine articular cartilage using a bipolar radiofrequency electrode. *Am J Sports Med,* 2000 September-October; 28(5):720-4. These devices do not accurately capture the multidimensional physiochemical occurrences of electrosurgery contemporaneously.

Further, fluid field impedance and fluid field capacitance sensing devices have been disclosed in prior art that allow feedback control of generator power output that drives the electrosurgical process, such as referenced in U.S. Pat. Nos. 6,306,134, 6,293,942, and the like. Energy delivery control is limited to these bulk properties which have yet to be accurately or completely correlated to the physiochemical governing relations of electrosurgery, and has proved to be too inaccurate relative to tissue response to serve as therapeutic benchmarking or controlling parameters.

However, as disclosed in U.S. patent application Ser. No. 10/119,671, the electrosurgical process is governed not by plasma or related forms of ionization but by electrolysis and oxy-hydro combustion. Therefore, development of electrosurgical devices and methods that are tailored to detect and measure the relevant parameters of electrolysis and oxy-hydro combustion are more appropriate and needed to enable desired treatment outcome. Clearly, there is a need for electrosurgical devices that are not only optimized to the true physical and chemical processes involved in the operation and use of such electrosurgical devices upon biologic tissue within safe energy spectra and power ranges, but also the need for the sensing and measurement of the true physiochemical occurrences of electrosurgery. Such devices will allow the more accurate and safe application of electromagnetic energy for electrosurgery to achieve intended outcomes.

Disclosed herein are two distinct means to accomplish these goals, which have heretofore not been contemplated or accomplished due to the lack of recognition of the electrolysis and oxy-hydro combustion process as inherent in electrosurgery: (1) the real-time simultaneous and contemporaneous detection and measurement of the relevant parameters of electrosurgery as described in the electrolysis and oxy-hydro combustion phenomena and (2) the placement of these detection and measurement devices within the surgical instrumentation itself, geographically juxtaposing sensing and measuring devices with treatment delivery devices, allowing for direct feedback of the treatment site to the medical practitioner.

BRIEF SUMMARY OF THE INVENTION

In one embodiment the invention provides an electrosurgical probe for performing electrosurgery, which probe includes an active electrode and a return electrode separated by an insulating member and means for sensing and transducing pH concentrations in proximity to the active electrode and return electrode. The means for sensing and transducing pH concentrations can include a miniature glass bulb and Ag—Cl sensing wire probe. The electrosurgical probe of the invention can further include an electrosurgical controller that incorporates the pH signal in control algorithms to meter power output to the active electrode.

In another embodiment the invention provides an electrosurgical probe for performing electrosurgery, which probe includes an elongated member with an active electrode and a return electrode separated by an insulating member at the distal end of such elongated member, with a thermoluminescent crystal generating a temperature signal positioned adjacent to the active electrode. The thermo-luminescent crystal can include a beacon insert within a larger insulating member. The thermo-luminescent crystal can be positioned so as to be immediately adjacent the active electrode. The electrosurgical probe can further include an electrosurgical controller that incorporates the temperature signal generated by the thermo-luminescent crystal in control algorithms to meter power output to the active electrode.

In yet another embodiment the invention provides an electrosurgical probe for performing electrosurgery, which probe includes an active electrode and a return electrode separated by an insulating member, and a conductivity metering device that generates a conductivity signal. The conductivity metering structure can be located adjacent to the active electrode. The electrosurgical probe can further include an electrosurgical controller that incorporates the conductivity signal in control algorithms to meter power output to the active electrode.

In yet another embodiment the invention provides an electrosurgical probe for performing electrosurgery, which probe includes an active electrode and a return electrode separated by an insulating member and an acoustic detector device that generates an acoustic signal, thereby detecting the electrolysis phenomena and rate. The electrosurgical probe can further include an electrosurgical controller that incorporates the acoustic signal in control algorithms to meter power output to the active electrode.

In yet another embodiment the invention provides an electrosurgical probe for performing electrosurgery, which probe includes an active electrode and a return electrode separated by an insulating member, and an ion sensor device generating an ion sensor signal. The electrosurgical probe can further include an electrosurgical controller that incorporates the ion sensor signal in control algorithms to meter power output to the active electrode.

In yet another embodiment the invention provides an electrosurgical probe for performing electrosurgery, which probe includes an active electrode and a return electrode separated by an insulating member, and a gas production sensor generating a gas production sensor signal. The electrosurgical probe can further include an electrosurgical controller that incorporates the gas production sensor signal in control algorithms to meter power output to the active electrode.

In yet another embodiment the invention provides an electrosurgical probe for performing electrosurgery, which probe includes an active electrode and a return electrode separated by an insulating member, and a thermoelectric semi-conductor generating a thermoelectric signal. The electrosurgical probe can further include an electrosurgical controller that incorporates the thermo-electric signal in control algorithms to meter power output to the active electrode.

In yet another embodiment the invention provides an electrosurgical probe for performing electrosurgery, which probe includes an active electrode and a return electrode separated by an insulating member, and a piezo-electric thin-film pyrometer generating a piezo-electric signal. The electrosurgical probe can further include an electrosurgical controller that incorporates the piezo-electric sensor signal in control algorithms to meter power output to the active electrode.

The invention further provides a method wherein sensing, measuring, and detecting one or more relevant parameters of electrosurgery is performed, thereby allowing increased treatment safety, efficacy, and allowing the ability to more effectively utilize either electrolysis and/or oxy hydro combustion reactions and phenomena that occur during electrosurgical application, wherein such use of electrolysis and/or oxy-hydro combustion that occurs during electrosurgical application is part of the treatment protocol.

A primary object of the present invention is to devices and methods relating to detection of one or more parameters relevant to electrolytic electrosurgery.

Another object is to provide detectors or sensors located proximal to the active electrode of an electrolytic electrosurgery probe.

Another object is to provide detectors or sensors disposed between an active electrode and a return electrode of an electrolytic electrosurgery probe.

Another object is to provide detectors or sensors located within a cavity or chamber wherein the active electrode of an electrolytic electrosurgery probe is disposed.

Another object is to provide detectors or sensors located within a variable volume cavity or chamber wherein the active electrode of an electrolytic electrosurgery probe is disposed.

Yet another object of the invention is to provide detectors or sensors for measuring one or more parameters including pH concentration, temperature, conductivity, impedance, ion concentrations, gas production or sound.

Yet another object of the invention is to provide control systems for controlling an electrolytic electrosurgery probe utilizing detectors or sensors determining one or more parameters relevant to electrolytic electrosurgery.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

Figure 1A:
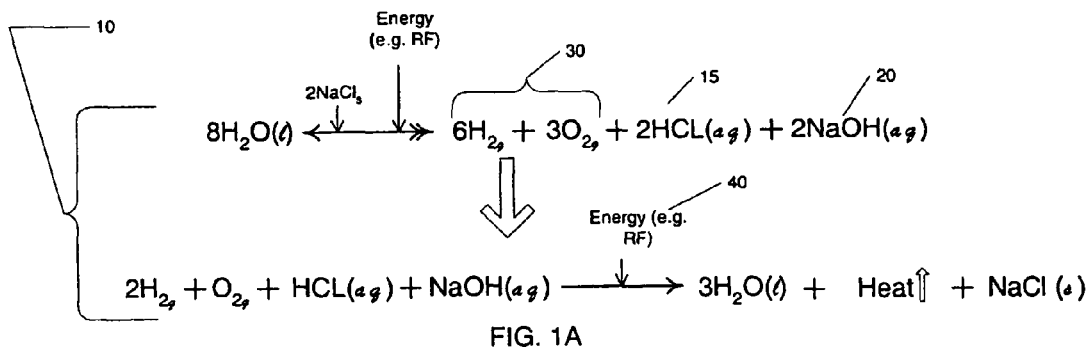
FIG. 1A is the stoichiometric chemical equation for chemical reactions related to the invention which govern the electrosurgical process.

For many years, the etiology of the phenomena observed in medical procedures utilizing radio frequency energy sources has been misidentified. As an example, in a recent publication, Stalder et al: Repetitive plasma discharges in saline solutions, *Applied Physics Letters, December* 2001, the electrosurgical condition expected during a standard electrosurgery procedure was tested. The authors describe photon emission from a saline solution as the hypothesized result of the formation of free electrons and positively charged ions interacting within a thin vapor envelope. Despite their contention and physiochemical hypothesis, it has become clear that this paradigm is incorrect. It is not possible that this phenomenon, should it exist at all, exists to a level responsible for the effects observed in electrosurgery. In fact, the contribution of a plasma to the treatment of organic matter in this instance is negligible as disclosed below. A more reasonable cause of the phenomena observed during electrosurgical procedures and applications, which more clearly fits the observations of Stadler et al, is the result of electrolysis and oxy-hydro combustion, as disclosed in U.S. patent application Ser. No. 10/119,671.

As further clarification of this disclosure, review of the definition of plasma, a definition that has become well accepted in the scientific community, is relevant. This review demonstrates that as medical applications have been developed utilizing radio frequency energy, misconceptions regarding the use of the term "plasma" have surfaced due to the common and traditional link between radio frequency energy and plasma formation in other settings.

It is no longer necessary to hesitantly state as many early and recent textbooks did and do that a fourth state of matter exists in the universe—referred to as a plasma. Ionizing radiation is ubiquitous in the universe and is most commonly witnessed as the fusion process in stars. The ubiquity of plasma becomes clear when the total abundance of all elements in the universe is considered as more than 99% of the universe's total mass exists within stars. The state of matter found in stars is considered to be this fourth state of matter, or plasma. Related to a gas by the general disorder and random distribution of particles, a plasma differs from ordinary gases in that its particles are mostly deficient of an electron, making them positive ions. In natural stable plasmas like the sun, stability is maintained by the enormous gravitational forces which contain the particles. The conditions found in stars of high temperatures and gravitational forces results in the only non-transient, stable, free natural plasmas known.

Plasmas formed in laboratories and those used for industrial applications such as metal fabrication are considered metastable, as the equilibrium state of the plasma components at standard pressure and temperature is one of the more commonly known states of matter, i.e. solid, liquid, or gas.

Without sustained input energy, plasmas normally self-quench and revert to one of these more stable states of matter via several processes. The most common of these processes is the recombination of a free electron with an ion dropping the total internal energy of the plasma below its normal "activation" energy; in most cases this results in the formation of a gas. A second common scenario is the attraction of the positive ions within the plasma to a negative ground. Positive ions will naturally flow toward the strong negative potential generated by the earth (lightning provides a commonly known example), similar to the conditions responsible for the movement of charge in electrical circuits.

As a result of the natural propensity of a plasma to self-quench via these processes, man-made plasmas must overcome these obstacles. This feat is typically accomplished by the steady input of energy into the plasma to constantly strip electrons from atoms and the confinement of both the electron and ion via a magnetic field (preventing the flow to ground). Man-made plasma formation is the result of either of two well-known processes, radio frequency coupling or heating. These two processes are fundamentally different but create the same effect of ion formation and preventative recombination. Plasmas generated by radio frequency sources use high frequency, high potential electromagnetic radiation to strip electrons from the outermost shells of the atoms in a gas. The energy coupled to plasma not only creates the ions and electrons, but also keeps them from recombining. In plasmas generated by high temperatures, large electrical currents are passed through filaments which results in heating. This heating actually causes electrons to "boil" off, by means of thermal excitation, the filament. The electrons then interact with the gas surrounding the filament, easily displacing electrons from their respective orbital sites, creating positively charged ions. The high temperature case is the effect observed in stars (a result of hydrogen-hydrogen fusion into helium), wherein the temperatures are high enough to both strip electrons from the gas and keep them from recombining. What becomes evident from observation of man-made plasma in the laboratory or industrial case is that very high energy must be continuously added to the system to maintain matter in the plasma state.

Yet another obstacle in the plasma paradigm of electrosurgery is the containment of the plasma as to prohibit the loss of charged particles to a ground plane so that they may be available for therapeutic effects. This containment is ordinarily accomplished by confining the electrons and ions in a magnetic field, so that when plasma is condensed, the efficiency of free electron and gas interaction cascades, thereby converting yet more gas into plasma. In vacuum conditions, a small partial pressure of gas can be excited to form a plasma with just one single electron. A single electron yields a cascade effect inducing secondary electrons which in turn generate a third and multiple generation electrons to the point where a sustainable plasma is created. This is dependent upon the total pressure of the system and the necessary confinement of the plasma to prevent self-quenching. Without these conditions it is unlikely that a plasma could be sustained or even form at all. In laboratory practice, man-made plasma begins within near ideal vacuum conditions and is constrained by high energy magnetic fields. In the industrial case, prolonged high energy input is required as in metal fabrication.

Superimposing the plasma paradigm in the surgical setting increases the already manifold constraints governing creation of a plasma. Liquids as encountered in either endoscopic or in vivo conditions typical of electrosurgical applications are not the ideal medium for plasma formation, as the energy needed to create an electron-ion pair is higher, as energy first must be used to break molecular bonds. In traditional plasmas, as mentioned above, a considerable amount of energy is needed to sustain a plasma for its intended purpose. In order to create and sustain a plasma condition in the body, itself constituted largely of water, it becomes evident that large amounts of energy would be needed. It can be calculated that the energy needed to cause tissue ablation, cutting, or coagulation, for example, via plasma would cause serious collateral harm to the patient. This circumstance provides a significant problem for the plasma paradigm of electrosurgery.

The following calculations illustrate that a "plasma" does not contribute significantly to the overall clinical effect of electrosurgery. The energy current needed to vaporize water and then sufficiently ionize the remaining molecules into a plasma is beyond the energy input of the electrosurgical system. Further, the electrosurgical system exhibits impedance rather than conductivity within the instrument effecter area.

The phenomenon of electrolysis and oxy-hydro combustion provides a more accurate alternative to the plasma paradigm. It is generally accepted that an electrosurgical probe system must create a "vapor pocket" immediately about the active electrode surface in order for any plasma-like activity to become evident. As an example, this requires the complete vaporization of a 0.9% by weight solution of sodium-chloride in deionized water. Any such dilute solution will result in a boiling point elevation and require additional energy input to reach the saturated vapor state. The typical boiling point elevations for such solutions range from 1%-5% and can be considered negligible for the purposes of this exercise (i.e. a saline solution will not boil at exactly 100° C., but rather on the order of 10° C. to 102° C. depending on the specific ambient pressure conditions of the fluid field). If we assume that water makes up the bulk of the components in question and look to the thermodynamic requirements to boil water on a per-pound-mass basis, it is known that:

$$m \cdot Cp_{H_2O} \cdot \Delta T = 1150.4 \frac{BTU}{Lb_m} = Q_{LHV}$$

When converted to Watts on a per second basis:

$$Q_{LHV} = 1213.7 \frac{kW}{Lb_m}$$

If we consider that the amount of fluid immediately surrounding the electrode tip is on the order of one-hundredth of a fluid ounce (0.01 oz.), then the energy of vaporization converted to a per-second basis is:

$$Q_{LHV} = 790 \frac{W}{(0.01)Oz.}$$

From this simple thermodynamic analysis, it is evident that given generic electrosurgical console output on the order of 180-260 W/sec, a large portion of the energy present is required to initiate vaporization at standard temperature and pressure (STP) conditions. This approximates 3 seconds of full power input to create an adequate vapor pocket for any "plasma" to begin forming. Furthermore, additional energy input beyond the latent heat of vaporization (LHV) is required to perform additional molecular excitations that would result in the stripping of electrons from the constituent atoms within the gaseous solution. It appears that a disproportionate amount of energy would be required to maintain the basic continual vaporization of water as it is continually refreshed in the surgical environment, i.e. not in a fixed pressure vessel, let alone perform higher energy dissociations of constituent sodium atoms.

In an alternative analysis, it is noted that plasma states of matter, as highly ionized gas conditions, are known to be excellent electrical and thermal conductors due to the rapid Brownian motion of the constituent atomic particles and freely available electrons for conduction of current. This suggests some specific behavioral characteristics which can be illustrated simply.

Given that the ionization energies of typical atomic elements can be expressed as:

$$X \rightarrow X^+ + e^-$$

and given that this value is known for sodium (D. W. Oxtoby, N. H. Nachtrieb. *Principles of Modern Chemistry*. Saunders College Publishing, N.Y., N.Y. 1986; pp. 438-439):

$$IE_1 = 496 \text{ kJ/mol}; IE_2 = 4562 \text{ kJ/mol}$$

and given that these values can be converted to Watts:

$$495,720 \frac{W \cdot Sec}{Mol}$$

Then given a 0.01 oz. estimate of the total volume of the saline fluid immediately surrounding the active electrode approximating the basic density of the fluid to be equivalent to that of water (a reasonable approximation), the mass of fluid can be calculated:

$$1.0443 \times 10^{-5} \text{ ft}^3 \cdot 62.4 \frac{Lb_m}{\text{ft}^3} = 6.48 \times 10^{-4} \text{ } Lb_m$$

At the standard solution content of 0.9% by weight NaCl:

$$6.48 \times 10^{-4} Lb_m \times 0.009 = 5.8 \times 10^{-6} Lb_m (NaCl)$$

Converting value to grams yields:

$$2.6 \times 10^{-3} \text{ gr(NaCl)}$$

Given the Molecular Weight of NaCl, 58.44 gr/mol, it is clear that only a fraction of a mole of the sodium chloride is present:

$$4.44 \times 10^{-5} = Y_{fraction}$$

By corollary, a similar order of magnitude fraction exists for sodium alone. Thus, it can be estimated that a $10^{-5}$ molar proportion of sodium is present at the electrode tip and would require additional ionization energy $IE_1$ on a per-second basis as follows:

$$496 \frac{kJ}{Mol} \cdot 1 \times 10^{-5} Mol(Na) = 4.95 \cdot Watts$$

This energy is in addition to that required to maintain continual vaporization of the saline fluid. Thus, the total minimum energy required to maintain any plasma-like activity immediately about the electrode tip can be described as the sum of $IE_1$ and LHV. Mathematically, on a per-second 0.01 oz. basis:

$$IE_1 + Q_{LHV} = 4.95 \cdot W + 790 \cdot W \approx 795 \cdot W$$

This result remains in discord with the fact that most common electrosurgical consoles are only capable of emitting 250 Watts of electrical energy. More than triple such energy is required to satisfy the thermodynamics of plasma creation.

Figure 13:
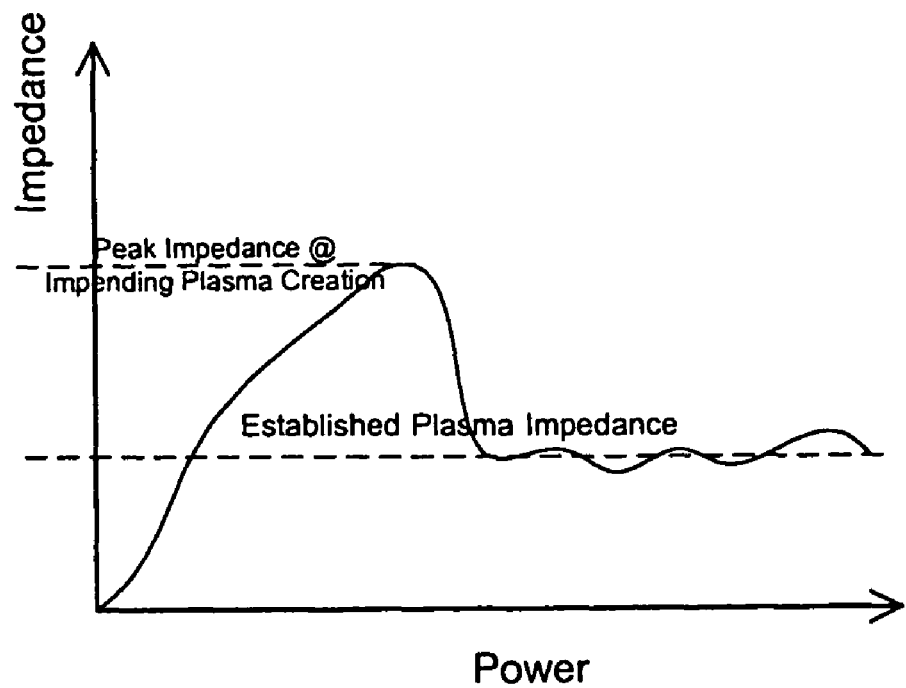
FIG. 13 is generic characteristic curve for a hypothetical impedance profile of an established plasma.
Figure 14:
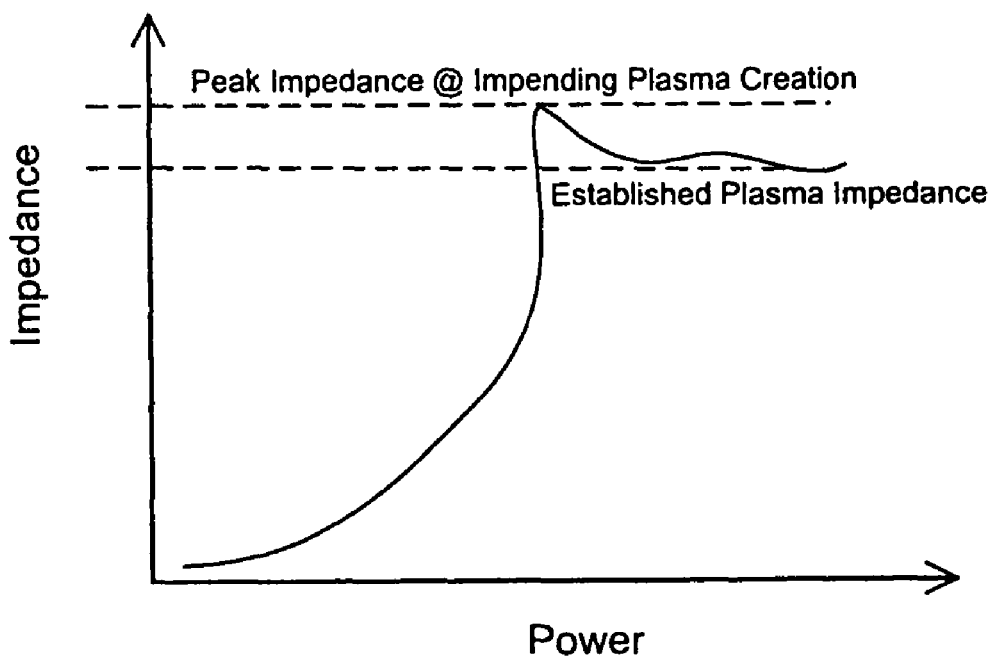
FIG. 14 is a generic characteristic curve for the impedance versus power of a typical immersed electrosurgical probe.

The electrical conduction characteristics of all plasmas are fairly well known and are most plainly called conductors. Plasmas do not exhibit high impedance characteristics that are common to simple gas volumes. Because they are highly ionized, there are sufficient free electrons to easily conduct current and as such do not provide significant impedance to current flow. A generic characteristic curve for a plasma's impedance profile once established is set forth in FIG. 13. The response curve of a typical electrosurgical probe from a power versus impedance standpoint is significantly different from typical plasma behavior. In the fluid state prior to "vapor pocket" formation, electrical conduction dominates the mode of transmission and impedance slowly rises with the temperature of the fluid. When vaporization results in nucleate boiling, the impedance begins a sharp rise and immediately "spikes" when full film boiling is initiated, i.e. the "vapor pocket." The characteristic curve for the impedance versus power of a typical immersed electrosurgical probe is as in FIG. 14.

It is evident that plasma would not behave electrically as does operation of an electrosurgical probe, because plasma would be an ideal conductor and show net reduced impedance to current flow once plasma was established. This is clearly not the case in the manifestation of a typical electrosurgical probe.

For the purposes of further analysis, the thermo-chemical approximations of water rather than a 0.9% NaCl aqueous solution can be utilized, again underestimating energy requirements, on the assumption that the initial state of the water starts out at approximately 25° C. and must result in full film boiling, approximately 100° C., to sustain the "vapor pocket" required for a "plasma." If the volume of water that is to be affected equals 0.3 cm³, then to initiate full film boiling:

$$Q_{SV} := \frac{Cp_{H2O}}{MW_{H2O}} \cdot (75 \text{ K}) \cdot 0.3 \text{ g}$$

Such that:

$$Q_{SV} = 94.073 \text{ J}$$

This is the energy input required to achieve the saturated liquid state. Insufficient energy exists to fully vaporize water; for that an additional energy input is required, the energy of vaporization or LHV. Therefore, further input of the following amount of energy is required (Lide D R, Ed. *CRC Handbook of Chemistry and Physics*. CRC Press, 83rd edition, 2002):

$$Q_{LHV} := 1150.4 \frac{\text{Btu}}{\text{lb}} \cdot 1055.5 \frac{\text{J}}{\text{Btu}} \cdot 1 \frac{\text{lb}}{453.6 \text{ g}} \cdot MW_{H2O}$$

Such that:

$$Q_{LHV} = 4.821 \times 10^4 \frac{\text{J}}{\text{mol}}$$

Thus, the total energy required to maintain a saturated "vapor pocket" would require a total energy input of:

$$Q_{input} := Q_{SV} + Q_{LHV} \cdot 0.3 \frac{\text{g}}{MW_{H2O}}$$

Such that:

$$Q_{input} = 897.146 \text{ J}$$

If it is assumed that it is actually plasma that is the driving force that will generate the 897.14 J required to vaporize the water, it is easy to evaluate the "plasma current" that is required to achieve this profile. The energy input would be required to produce EV particles in at least the quantity of the LHV and actually requires additional energy beyond this as the water is consuming it in a change of state process. Thus, using the LHV as a benchmark for the energy input, as it is the absolute minimum requirement for a plasma, it then follows that the actual number of elementary charged particles required to vaporize the 0.3 g sample of water is:

$$\frac{Q_{input}}{eV} = 5.6 \times 10^{21} \text{ particle}$$

using the average energy/particle=1 KeV, which is based upon the average electric field to which all the particles would be subject. This value is equivalent to the field produced by a typical electrosurgical generator at full power where Vpk-pk~1 kV or 1 keV. To properly account for the aggregate charge of the particles, the total number of particles is divided by 1,000, thus yielding:

$$\frac{Q_{input}}{eV \cdot 1000} = 5.6 \times 10^{18} \text{ particle}$$

1 keV particles at the ambient electric field strength produced by a typical electrosurgical generator, which is a fraction of a coulomb as follows:

$$\frac{Q_{input}}{eV \cdot 1000 \cdot ParticlesperCoulomb} = 0.897 \text{ C}$$

or:

$$\frac{Q_{input}}{eV \cdot 1000 \cdot ParticlesperCoulomb} = 0.897 \text{ s A}$$

This value can be classified on a per second basis as 0.9 Amp of "Arc-Current" (an extremely high current flow for an arc). It is clear that with approximately 90% of a Coulomb of charged particles there is ample availability for conducting electricity. In fact, at such a high concentration of charged particles the net resistance of any such volume would be extremely low. This finding conflicts with the behavior of the typical electrosurgical probe which exhibits a "capacitor" like behavior at the point of "plasma-like" transition. Such behavior should not be present with nearly a Coulomb of particles to conduct current. The net resistance of the system should drop at the point of plasma formation to near zero.

Figure 5A:
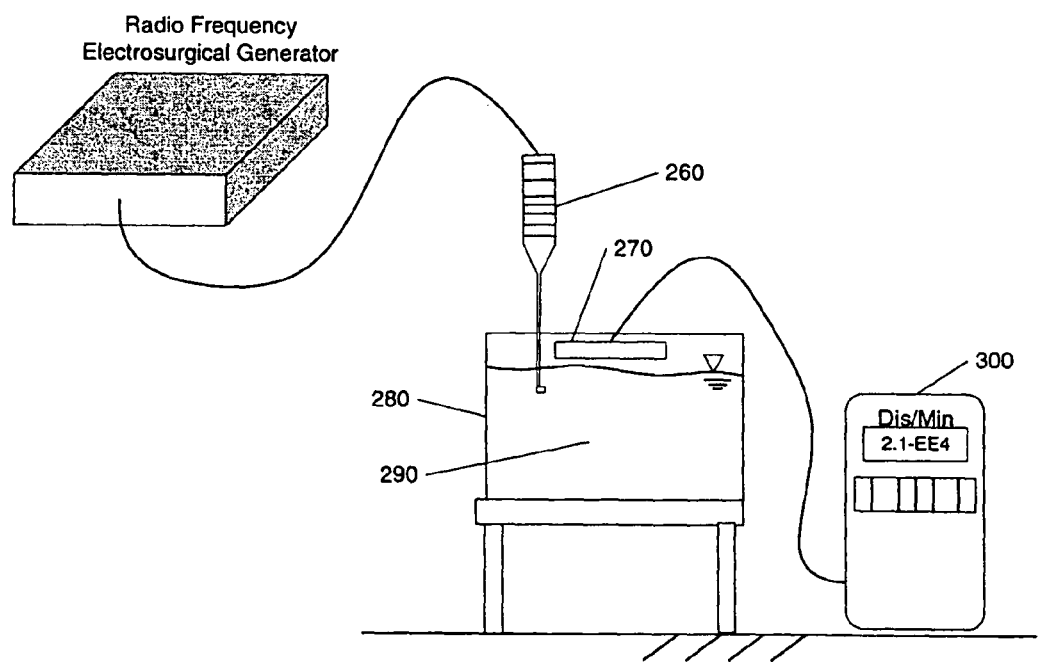
FIG. 5A is a view of an experimental apparatus set-up using an electrosurgical probe and an ionizing radiation detector.
Figure 5B:
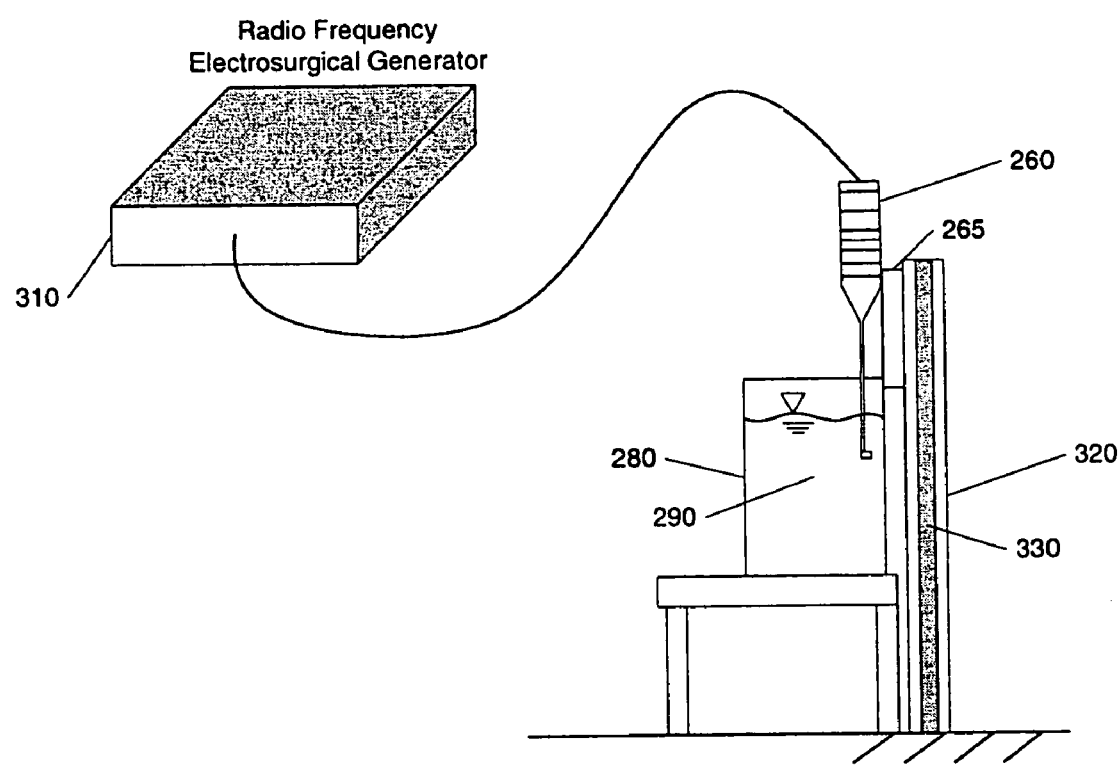
FIG. 5B is a view of a time integration experiment utilizing x-ray sensitive film for 30 minutes.

With this background information at hand, a series of experiments was conducted to further clarify the relevant parameters of electrosurgery, as disclosed in FIGS. 5A and 5B, which is centered on the electrolysis and oxy-hydro combustion physiochemical process in order to develop methods and devices for the detection and measurement of the relevant parameters of electrosurgery. Specifically, experiments were designed and performed to determine the existence and relative strengths of low level ionizing radiation if any, present within the electrosurgical process.

In one protocol, illustrated in FIG. 5A, the presence of ionizing radiation that might be produced in a saline solution (0.9% NaCl) with a standard electrosurgery tool was measured using radiation detector probe 270 and particle detector measuring and display unit 300 to monitor the treatment field for x-ray generation. Industrially accepted electrosurgical generator 310, set at a power setting of 900 Volts peak to peak at 460 kHz±1% and 245 Watts nominal maximum output power, was utilized, representing a relatively high energy configuration typically utilized in an ablation mode of electrosurgical operation. This high energy level was utilized to create the most advantageous situation for ionizing radiation to form if possible. Bi-polar electrosurgical probe 260 was activated, using radiofrequency electrosurgical generator 310 in 0.9% by weight sodium chloride solution 290 in glass reservoir 280 until a yellow discharge optical emission was observed as described in Stalder et al. This color is more correctly described (as opposed to the consideration of Stalder et al. discussed above) as the result of electron excitation, not to be confused with electron loss, and shows the standard color associated with the 590 nm wavelength light as depicted with optical emission instrumentation. Radiation detector 270, connected to particle detector measuring and display unit 300, sensitive to 200 disintegrations per minute, was mounted on the beaker adjacent to the probe 260 in solution 290. As discussed above, any plasma formation, even at a low scale, would result in free electron ion pairs and the release of low energy x-rays, due to liquid/electron interface interactions. Considering that the potential low energy x-rays that might be generated in the experimental apparatus would not have significant energy to penetrate glass electrolyte reservoir 280, radiation detector 270 was placed approximately 1 mm away from the air-water interface when probe 260 was activated. At this distance, 0.5 keV x-rays would be transmitted. Should a plasma be formed by electrosurgical probe 260 in any appreciable quantity above normal background radiation, the resultant ion-electron/solid interaction would result in the generation of x-rays. X-rays can be generated when an electron loses energy or when bound electrons in atomic shells are removed by ionizing radiation. The removal of shell electrons emits a characteristic x-ray with energies from a few keV to over 100 keV. Characteristic x-ray production for oxygen and sodium, for example, are below one keV. The slowing or break-off of the electrons results in white radiation or bremsstrahlung photons. These photons would have a range of energies on the same magnitude of the characteristic elemental x-rays. During light emission of the electrosurgical process, no detectable x-rays were sensed by radiation detector 270. Radiation detector 270, sensitive to 1 mrem/hour (200 disintegrations per minute), indicated no radiation above standard background radiation in which all tissue resides on earth. Since background radiation exposure averages approximately 2.5 milli-Sivert (0.01 SV=1 rem; $2.5 \times 10^{-3}$ Sivert=$2.5 \times 10^{-5}$ rem), 80% of which is natural radiation (half of which is due to radon) and 20% is man-made, ionizing radiation at those levels that might develop during electrosurgical procedures is irrelevant to treatment protocols.

FIG. 5B illustrates an additional experiment that was performed using unexposed x-ray film 330 in x-ray film case 320 to integrate a time exposure function that radiation detector 270 might have been unable to detect. Again a power setting of 900 Volts peak to peak at 460 kHz±1% and 245 Watts nominal maximum output power was utilized from electrosurgical generator 310 to energize probe 260. Fluid reservoir 280 was filled with 0.9% by weight NaCl solution 290 and probe 260 was fully immersed and placed within 1 mm of the glass wall of the reservoir. Probe 260 was then activated, and the normal yellow discharge became visible. Probe 260 was fired for 30 continuous minutes allowing any high energy phenomenon, if present, to present itself by allowing any high energy particles, x-rays, or free electrons escaping from the active electrode area to integrate over time and thus expose the film. Control source 265 of alpha ($\alpha$) particles was adhesively affixed to x-ray film case 320 to demonstrate exposure to the film from high energy particles penetrating the film case for an extended period of time. After 30 minutes of exposure to both the firing probe and control $\alpha$-particle source 265 only the area exposed to $\alpha$-particle source 265 was exposed. The film area immediately adjacent to the electrode remained unexposed and clear of any image.

These experimental results, based upon the premise that ionizing radiation will produce detectable x-rays exceeding background levels, invalidate plasma formation as a means to achieve the effects of the electrosurgical process. Single ionizing events may occur on a theoretical basis, but would do so at a limit well below detection, and certainly would not be sufficient for any tissue treatment protocol. As an example, a theoretical mathematical exercise was conducted in which the assumption was made that plasma actually does form at a maximum energy level equal to background levels of 200 dpm (disintegrations/minute) or 3 dps (disintegrations/second). In the experimental set-up, it was estimated that the air-water interface reduced the total transmittance by a factor of 100 and the solid angle effect of the detector accounted for another factor of 1000 reduction. Using the transmittance reducing elements to estimate the disintegrations per minute of the plasma at its core, then we have ($10^2 \times 10^3 \times 10^1 \times 60$ dps/dpm) or [air/water interface reduction]×[solid angle detector effect]×[nominal background level order of magnitude]×[min to sec. Conversion of 10], or a value of $10^7$ dps, which is approximated as an x-ray yield from the electrosurgical tool during discharge. If each x-ray is the result of a single charged particle or free electron/solid interaction, which is a gross idealization erring on the side of higher charged particle/x-ray ratio, a maximum amount of ionized particles of $10^7$ is possible. We know the energy of the charged particle is on the order of 1 keV, or approximately $10^{-16}$ Joules per particle. Multiplying the total ideal theoretically available particles by the maximum energy per particle ($10^7 \times 10^{-16}$) yields a total energy per second capacity on the order of $10^{-9}$ J, or a nano-Watt for the ion component. Since charged particles at 1 keV would travel no more than 100 Å, the total effected volume would be extremely and impracticably small. Since gross observation of the electrosurgical process and its function clearly demonstrate effects of the probe at ranges past a centimeter, the effects of an electrosurgical apparatus typically utilized for medical treatments cannot be due to such low level ionizing radiation, if it exists at all, as demonstrated by distances employed in practice. Theoretical single or small scale random and uncontrollable ionization events would be more reasonable terminology to describe any such creation of ions and electrons in the solution relative to treatment goals rather than plasma formation for those so inclined. Since the creation of ionizing radiation is not detectable above background radiation noise in which all tissue resides here on earth, the mechanism for electrosurgical procedures and the corresponding tissues effects are unrelated to these hypothetically proposed low level ionizing radiation occurrences.

Further, evaluation of the well known interaction of ionizing radiation with cells adds more evidence that ionizing radiation does not play a role in the electrosurgical treatment process. Ionizing radiation when applied to cells or tissue leads to molecular changes and to the formation of chemical species that are damaging to cellular constituents, such as chromosomal material. Such damage leads to irreversible alterations in the function and construction of the cell itself, damage that is readily observed histologically. The process that occurs when ionizing radiation is applied to the cell begins with conversion of water after $\sim 10^{-16}$ seconds. This is depicted as $H_2O \rightarrow H_2O^+ + e^-$ with the application of ionizing radiation. The next occurrences are as follows over the next $\sim 10^{-6}$ seconds: $H_2O^+ \rightarrow H^+ + OH$; $H_2O + e^- \rightarrow H_2O^-$; $H_2O^- \rightarrow H + OH^-$. H and OH are considered free radicals and participate in further reactions. The most prominent is the formation of hydrogen peroxide as follows: $OH + OH \rightarrow H_2O_2$. These products react with the organic constituents of the cell and tissue, such as nucleic acids and hydrogen extraction from pentose, to release organic free radicals induced by radiation damage. Histological evidence of the electrosurgical process as disclosed in U.S. patent application Ser. No. 10/119,671 clearly does not provide evidence of radiation induced tissue damage at any level of linear energy transfer. Histological evidence demonstrates levels of necrosis, such as karyorrhexis and nuclear picnosis at one end of the spectrum to frank necrosis or vaporization at the other end of the spectrum, as would be expected from electrolysis and oxyhydro combustion. It would be expected that any ionizing radiation effects, should they occur in electrosurgery, would have manifested themselves long term as local radiation injury, given that electrosurgical methods and devices have been in wide spread use for over 50 years. The disparity between the description of electrosurgery in the prior art as governed by plasma formation and/or ionizing radiation and concerns for the induction of ionizing radiation-related disease is readily apparent in prior art and the medical literature. This evaluation of radiation induced cellular and tissue changes adds additional evidence that sensing and measuring devices developed for the relevant parameters of electrosurgery would not include those that may detect hypothetical and necessarily irrelevant low level ionizing radiation.

The foregoing disclosure helps to define the relevant parameters of electrosurgery as related to electrolysis and oxy-hydro combustion as disclosed hereafter.

The equations of FIG. 1A illustrate the chemical equations that describe the overall oxy-hydro reaction, with associated acid-base shifts, resulting from electrolysis of water and subsequent ignition of the resulting oxygen and hydrogen. The physiochemistry of the electrosurgical process consists of an acid-base shift that governs the relative availability of the amount of water that can be consumed as part of an electrolysis chemical reaction. The electrolysis reaction is driven by the high frequency current flowing between active and return electrodes in both the bi-polar and mono-polar modes of operation of electrosurgical probes. This oxy-hydro combustion theory accounts for all necessary chemical and energy constituents that are present as well as the physical observations of light emission and heat generation during the use of such devices. This description reconciles the physiochemical occurrences of electrosurgery into a single accurate and cohesive theory.

Chemical equations 10 generally govern the process, whereby the initial liberation of elemental oxygen and hydrogen gases 30 occurs by means of electrolysis. Given that the underwater electrosurgical process occurs in a salt solution, either that applied as an irrigant or that of the tissue or cell itself, such as a 0.9% by weight saline solution, the true role of these elements has been reconciled. The presence and true action of the salt, such as sodium chloride (NaCl), can be accounted for by means of equations 10. The normal stoichiometry of the electrolysis reaction dictates that if elemental gas separation is occurring, then the solute participants must join with the remaining solution components of water to form a complementary acid-base pair. This pair is shown on the right-hand side of the upper half of equations 10 as hydrochloric acid 15 and sodium hydroxide 20 base pair. As is well known, hydrogen and oxygen gases 30 can be co-mingled without spontaneous exothermic reaction. A small amount of energy, such as RF energy 40, is required to initiate the nominally endothermic reaction and ignite the oxy-hydro combustion. Once ignited, the reaction will continue until all the reactants are consumed and reduced to the products shown on the right-hand side of the lower half of equations 10.

Figure 1B:
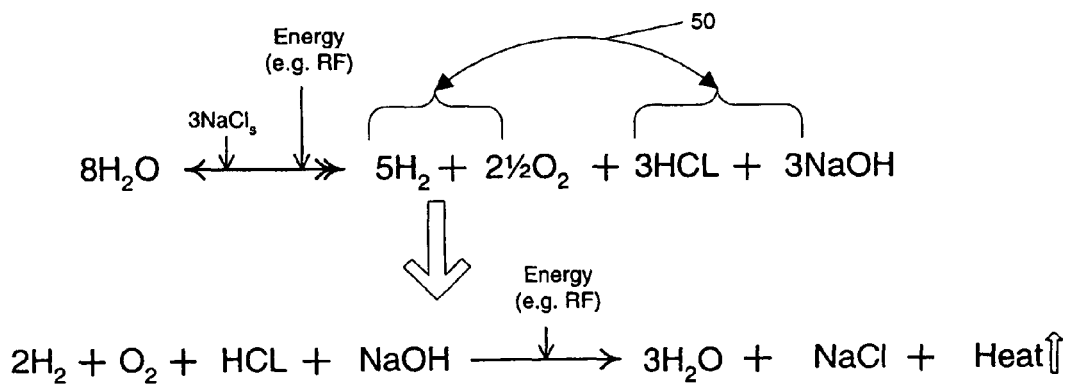
FIG. 1B is the equation for and a view of the acid-base "throttle" effect.

The equations of FIG. 1B illustrate the effect of the acid-base throttling reaction. The oxy-hydro combustion process depicted is dynamic and occurs in a fixed fluid reservoir, which necessarily results in dynamically changing concentrations of salt ions as a function of electrolytic conversion of water to elemental gas. This equation necessarily suggests that as the acid-base shift occurs in the reservoir, less and less water is available for electrolysis. This phenomenon is seen in FIG. 1B where acid-base pair 15 and 20 is shown in increased molar proportion to the normal stoichiometric quantity of base reactions 10. The reduction of available water for electrolysis is evident in relationship 50 of oxygen and hydrogen gas to the acid-base pair. The finding is necessarily evident from the stoichiometry, namely that insufficient water is available given a fixed initial eight (8) moles of water, based on the finite reservoir of water, with increasing resulting molar concentrations of acid and base as oxygen and hydrogen are liberated from the solution in a gaseous state, such as by bubbling out of solution. As fewer moles of oxygen and hydrogen gas are present after electrolysis as in FIG. 1B, the balancing portion of atoms account for the dynamic increase acid-base concentration.

Figure 1C:
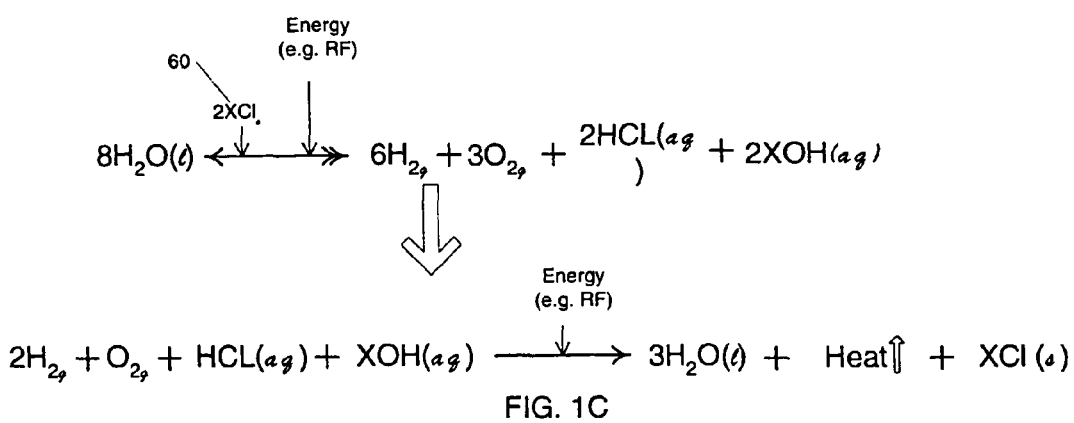
FIG. 1C is the equation for and a view of the generalized form of the electrolysis and oxy-hydro combustion reaction process.

The equations of FIG. 1C demonstrate a more general case of the electrolysis and oxy-hydro combustion reaction process in which the ionic salt is represented by variable 60, where X is any appropriate group I, period 1-7 element of the periodic table. This generalized reaction illustrates how hydronium and hydroxide ions can contribute to the same overall chemical reaction known as electrolysis and oxy-hydro combustion.

Figure 1D:
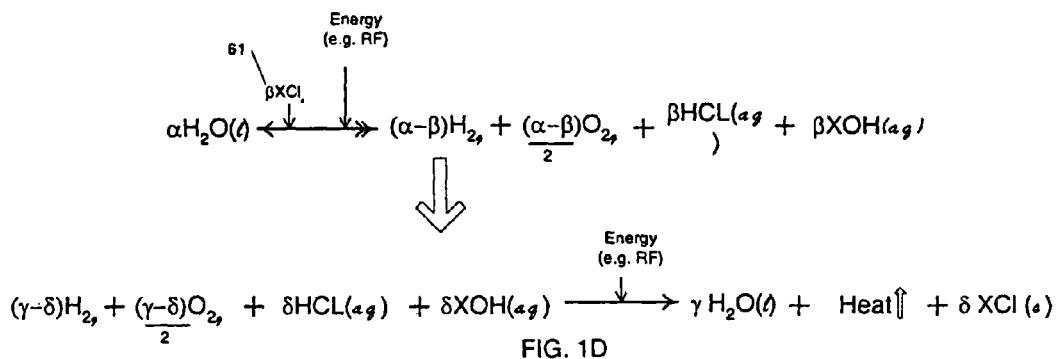
FIG. 1D is the equation for and a view of the generalized form of the electrolysis and oxy-hydro combustion reaction process showing the effect of varying molar coefficients.

The equations of FIG. 1D demonstrate the more general case of the electrolysis and oxy-hydro combustion reaction process in which the ionic salt is represented by variables 61, consisting of $\alpha$, $\beta$, $\gamma$, and $\delta$; wherein, the molar quantities required for stoichiometric combustion are any value that appropriately satisfies the oxidation reduction valence requirements for the overall reaction. This generalized reaction case shows how oxygen and hydrogen requirements can vary and still result in the same overall chemical reaction known as electrolysis and oxy-hydro combustion.

The modes of electrolysis and oxy-hydro combustion operation described in FIG. 1A, FIG. 1B and FIG. 1C depict theoretical stoichiometric reaction processes induced by application of high frequency electromagnetic energy to a salt ion solution, including salt ion solutions typically found within biologic tissues themselves. The fundamental process is governed by the rate of electrolysis in the initial dissociation of water into oxygen and hydrogen gas, as shown in equations 10.

Figure 2A:
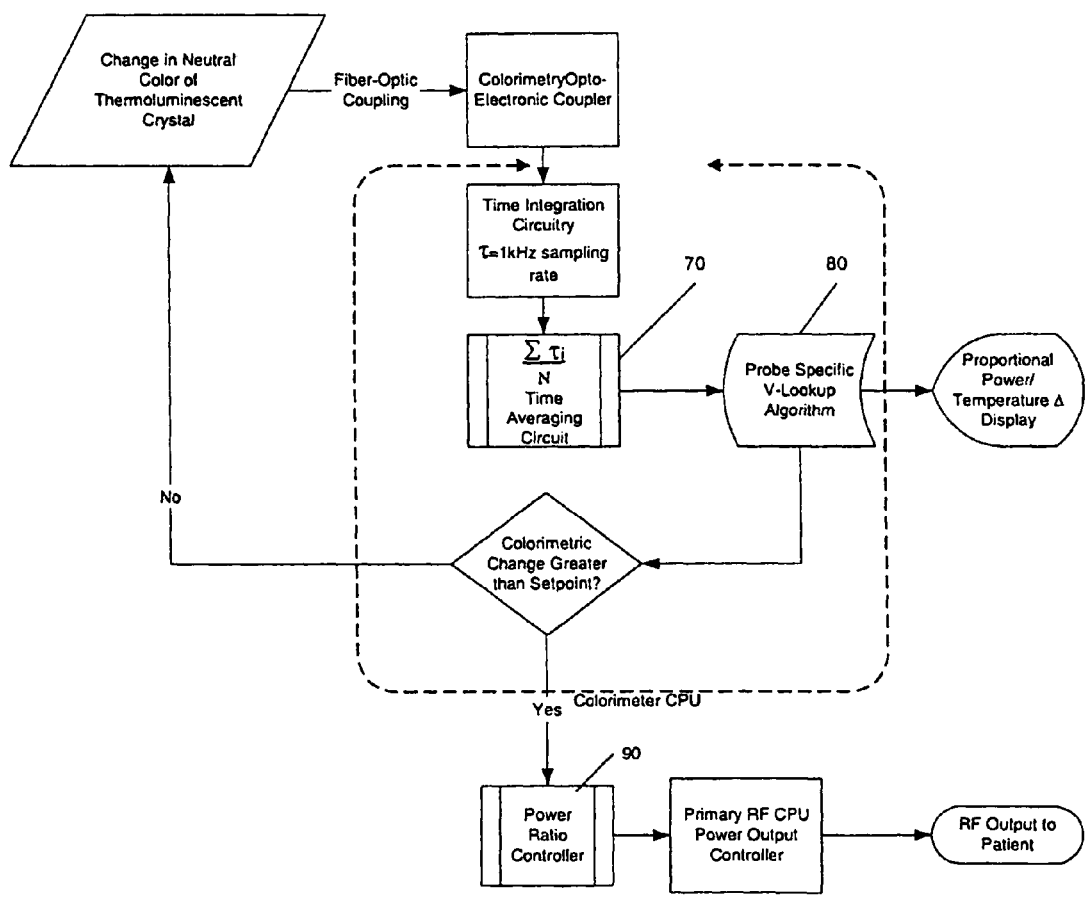
FIG. 2A is a flowchart for a control logic of the invention provided by the sensing and control systems and the relevant decision/action points for a thermoluminescent crystal monitoring system.
Figure 2B:
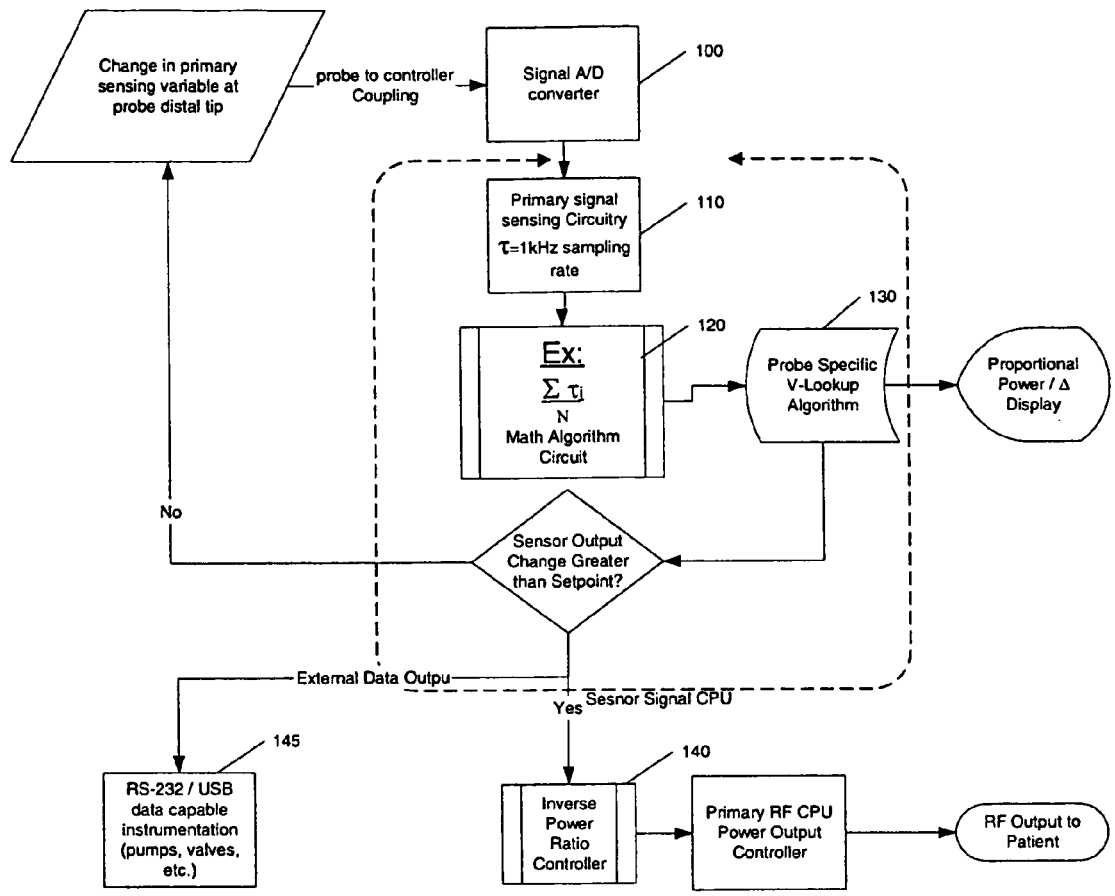
FIG. 2B is a flowchart for a control logic of the invention provided by the sensing and control systems and the relevant decision/action points for a generalized monitoring system.
Figure 3:
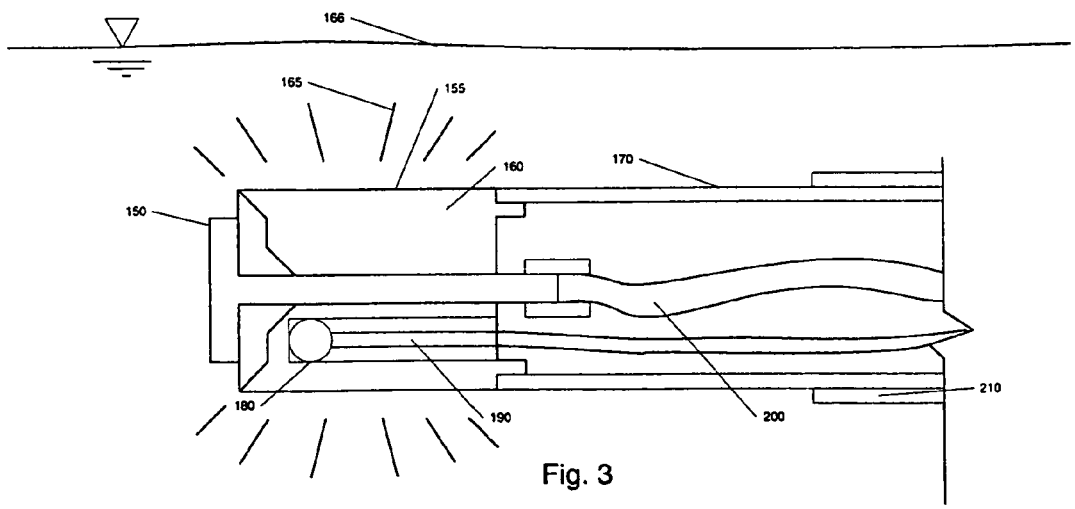
FIG. 3 is a view of the cross section of a probe of the invention with a thermo-luminescent crystal sensing system resident on the distal tip.

A preferred embodiment of the present invention disclosed herein is use of thermo-luminescent crystals 160 as depicted in FIG. 3. An example of crystals that demonstrate linear temperature to luminescent profiles are described in Buenfil AE et al. Dosimetric Properties of europium-doped potassium bromide thermoluminescent crystals. *Health Physics*, Vol. 62(4):341-343, 1992. Crystal 160 is an encapsulated thermo-luminescent crystal in thin-walled zirconia shell 155, with a nominal thickness of 0.0001-0.002", providing shielding against thermo-chemical degradation of the potassium bromide crystal in harsh immersion environments, as shown in FIG. 3. FIG. 3 thus depicts an electrosurgical probe immersed in electrolyzable aqueous media 166. In the probe, active electrode 150 is connected to active conductor wire 200, which in turn is connected to a power supply. The power supply, for this and all other embodiments presented herein, can provide radiofrequency energy at any frequency, and can alternatively supply direct current energy, pulsed direct current energy, or the like. The probe is partially encased within insulating sheath 210, with exterior return electrode 170. In operation, light 165 is emitted from thermoluminescent crystal 160 in response to generated heat. The detector system can further include fiber optic element ball ended lens 180 connected to light sensing optical fiber 190, located such that only light generated by crystal 160 is accumulated by lens 180. The creation of such a device is possible through one of several means by which zirconia is deposited on the surface of the thermoluminescent crystal and subsequently hardened, or alternatively by a simple double barrel pulse injection molding procedure familiar to those skilled in that art. Use of super-plastic zirconia ceramic alloys is beneficial to avoid green-to-cured state contraction in molecular spacing as theoretical density limits are achieved through the kilning process used to cure the ceramic. As geometric reductions of 20-30% are normal for ordinary zirconium alloys, this can be easily offset by the 100-150% elongation capabilities of a superplastic alloy of zirconium. Kim B N et al. A High Strain-Rate Superplastic Ceramic. *Nature*, Vol. 413, $20^{th}$ September, 2001, pp. 288. As the thin-walled protective shield of zirconia is thin enough to be semi-transparent at such cross-sectional area, the color-shift of the glow-curve of the thermoluminescent crystal is easily visible through the zirconia and can be visibly detected by the human eye under ordinary lighting conditions. Console control algorithms 120 and 130, FIG. 2A and FIG. 2B, are fed an input signal from ball lens fiber optic element 180 in FIG. 3, which is used to transmit the luminescence from the temperature sensitive crystal to a photo-detector or calorimeter. The photo-luminescence is transformed via analog to digital flip-flop circuitry into a digital signal of streaming data and recorded in time integration sampling circuitry, well known to those skilled in the art of real-time data sampling. The data stream is modified by numerical software algorithms 70 to provide a stable control variable. The stable control variable is used in traditional data comparison algorithms 80 to perform electrosurgical console radiofrequency power output "throttling" via inverse proportionality control circuitry 90, well known to those skilled in the art of power output control systems. The circuitry performs real-time correlation of sensed color shifts by the thermoluminescent crystal in response to temperature changes on the surface of the probe tip. The optical fiber is placed immediately sub-surficial to the exterior of the electrode-insulating member such that a focusing "lens-effect" is utilized to transmit the thermo-luminescent crystal color to the control circuitry.

Yet another embodiment is the use of thermoluminescent crystal material, such as those described above, as depicted in FIG. 10 where the thermoluminescent crystal material is used as an insert for thermoluminescent crystal "beacon" 440 within the insulator in a bore at the extreme distal end of the insulator where the active site of the electrosurgical device exists. When the thermoluminescent crystal is formulated in a manner such that the chemical structure of the crystal is hydrophobic (by way of example an optically clear silica glass deposition coating may be applied to the crystal which does not dissolve in aqueous environments), the crystal can actually become external to the insulator and provide combined feedback of device and treatment site temperatures. In one alteration of the chemistry, europium doping of zirconia-yttrium ceramic can be employed such that the thermoluminescent function becomes that of ceramic insulator 450 itself.

Figure 4:
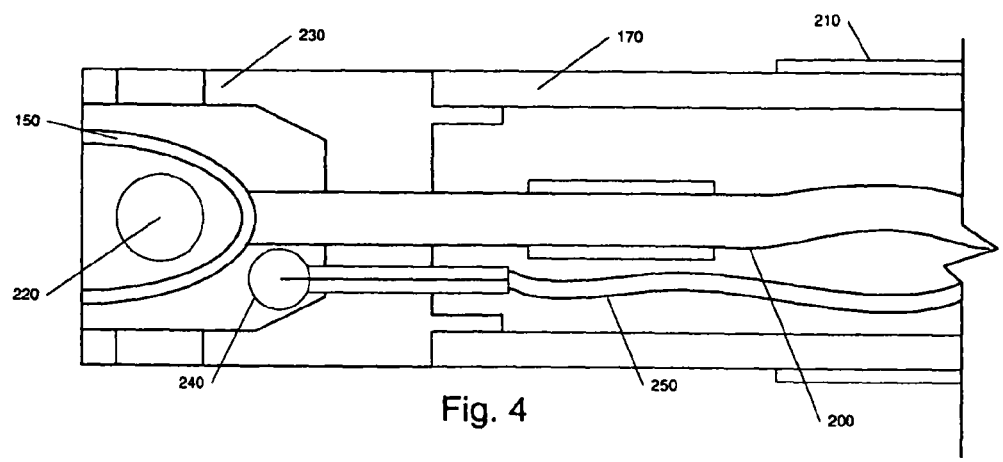
FIG. 4 is a view of the cross section of a probe of the invention with a pH sensing system resident on the distal tip.

Yet another embodiment is shown in FIG. 4 wherein use of an instrument integrated pH monitoring system comprising a reference potential and use of glass bulb capacitive pH detector 240 is described. The micro glass bulb detector 240 is connected to pH potential conductor wire 250. In the embodiment depicted in FIG. 4, the probe, further comprises europium-doped thermoluminescent yttria-stabilized-zirconia insulating member 230 for temperature detection, and acid/base shift fluid outflow portal 220, it being understood that these elements represent alternative embodiments. The pH monitoring system is coupled via electrical connection 250 to control circuitry for governing multiple parameters of the electrosurgical environment. FIG. 2B depicts such circuitry providing both differential feedback for electrosurgical console output parameters 140 and integral feed-forward control 145 of adjunct devices that can provide additional inputs to the surgical field, such as surgical irrigation systems and pumps for irrigation systems, as disclosed in U.S. patent application Ser. No. 10/157,651, entitled Biologically Enhanced Irrigants, filed May 28, 2002. For example, measurement of pH has been determined to be an effective method to monitor the electrolysis that occurs in tissue. Guy Finch J et al. Liver electrolysis: pH can reliably monitor the extent of hepatic ablation in pigs. *Clin Sci (Lond)* 2000; 102(4):389-395.

Figure 6:
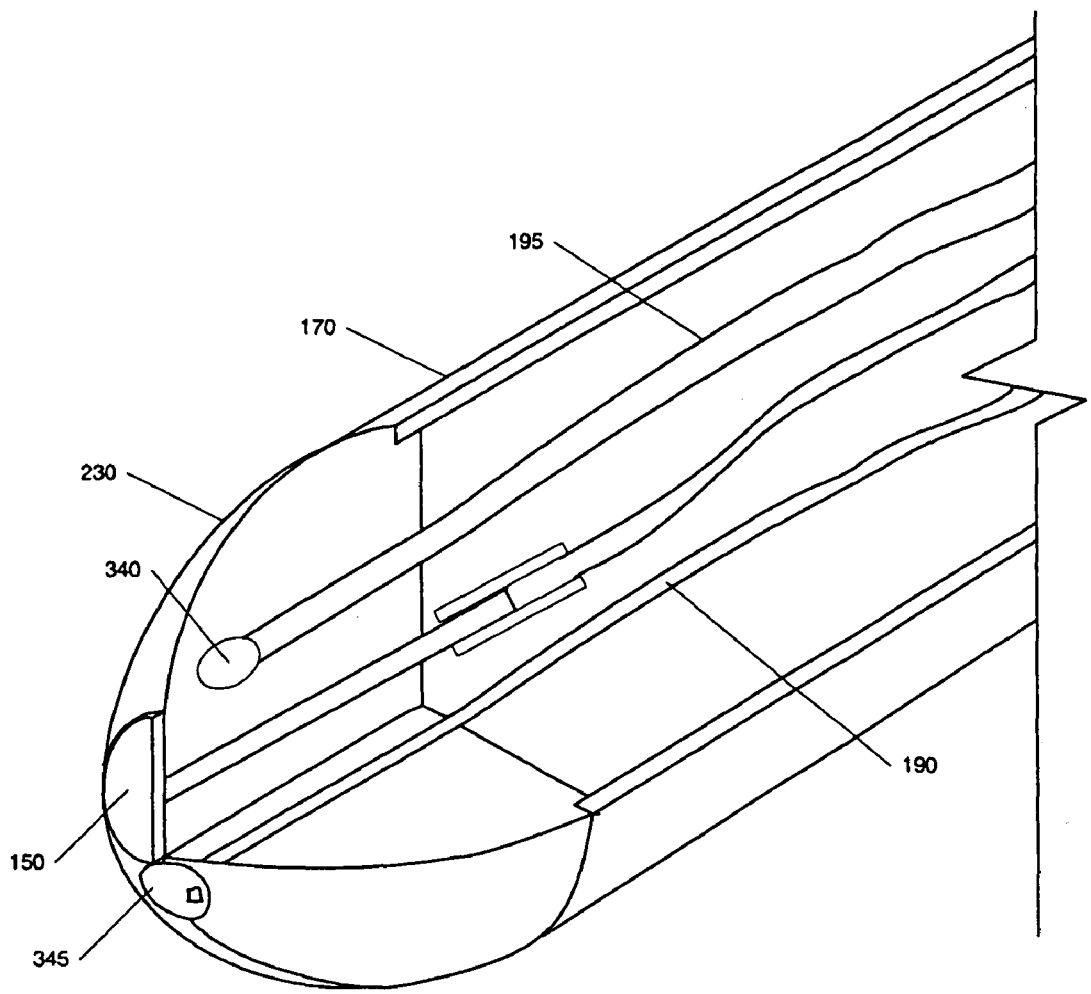
FIG. 6 is a view of a probe of the invention with a fiber-optic sensing array for utilizing FTIR, GFCR, and optical pyrometric algorithms and circuitry for governing electrosurgical processes.

FIG. 6 illustrates yet another embodiment of the configuration of an electrosurgical probe wherein the distal tip insulator includes a thermo-luminescent crystal 230 and contains an array of multiple independent optical fibers 190 and 195 configured to provide a distributed profile of surgical site field conditions. Each independent optical fiber is a single or multi-mode fiber utilizing "ball-end" focusing lens 340 and 345 to provide means for viewing and determining "free-field" bulk property conditions at a predetermined focal length external to the probe, thermo-luminescence colorimetry/thermometry at the surface of the probe, and oxygen and hydrogen gas production using gas filter correlation radiometry or Fourier infra-red spectroscopy through optical switching performed within the control unit. In one embodiment, the methods disclosed in U.S. Pat. No. 5,128,797 can be employed.

Figure 7A:
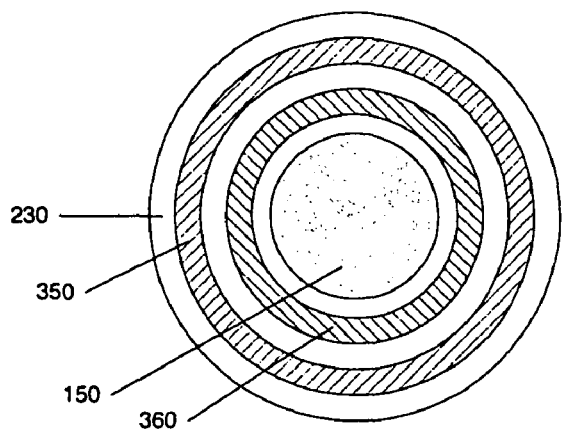
FIGS. 7A and 7B are views of a probe of the invention with a conductivity sensor at the distal tip for sensing acid-base shifts at the locality of the surgical site.
Figure 7B:
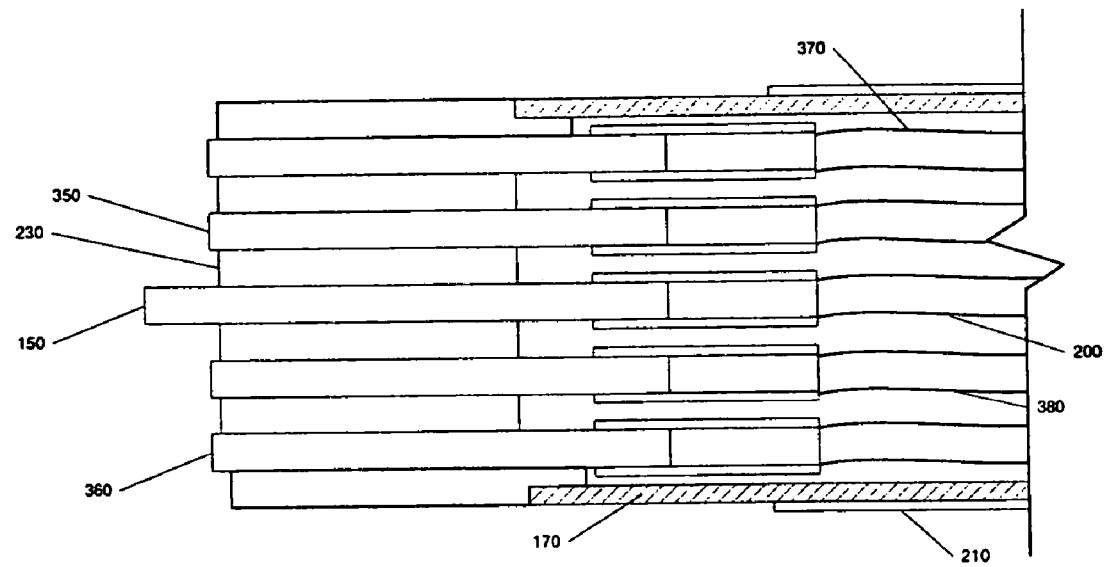

FIG. 7A and FIG. 7B depict yet another embodiment of an electrosurgical probe comprising a distal active electrode 150 and a proximal return electrode 170 separated by an insulator wherein is disposed conductivity meter pair electrodes 350 and 360 for sensing acid-base shifts due to the byproducts of electrolysis induced by electrosurgery. Cylindrical conductivity electrode 350 is electrically connected to conductivity sensing voltage conductor wire 380, and electrode 360 is similarly connected to wire 370, it being understood that either electrode 350 or electrode 360 can serve as a reference electrode. In FIGS. 7 and 7A, insulating member 230 is provided, which may optionally be an europium-doped thermoluminescent yttria-stabilized-zirconia insulating member. The conductivity meter is electrically coupled to proportionality circuitry 140 for providing both differential feedback for electrosurgical console output parameters and integral feed-forward control 145 of adjunct devices that can provide additional inputs to the surgical field, such as surgical irrigation systems and pumps similar to those disclosed in U.S. patent application Ser. No. 10/157,651.

Figure 8:
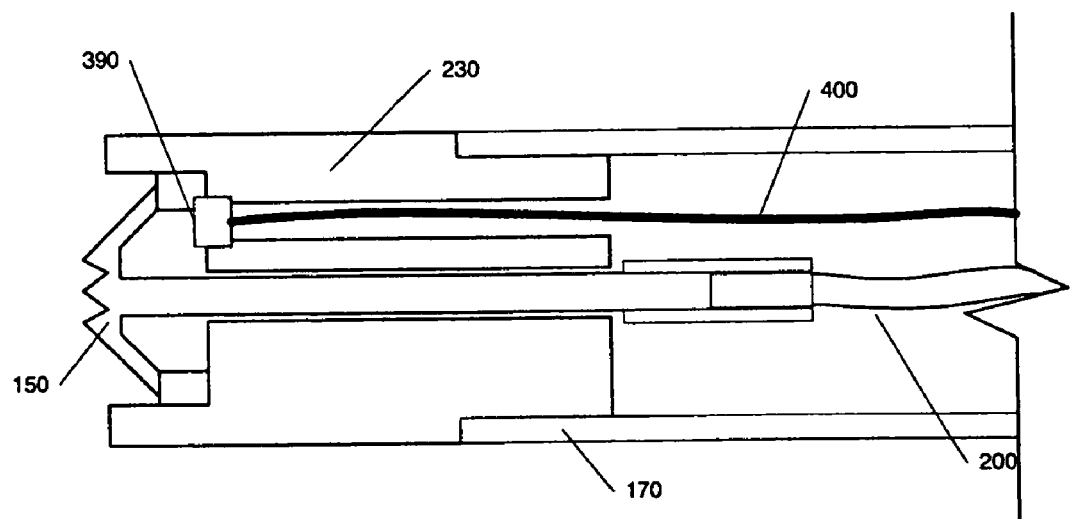
FIG. 8 is a view of a probe of the invention with a piezo-acoustic sensor for detecting oxy-hydro combustion zone sound shift and providing a feedback measurement for governing electrosurgical processes.

FIG. 8 depicts yet another embodiment of an electrosurgical probe including a distal active electrode and a proximal return electrode separated by an insulator wherein is disposed piezo-acoustic sensor 390 positioned on the surface of the insulator and connected by means of conductor wire 400. Piezo-acoustic sensor 390 may, in one embodiment, be a piezo-acoustic drum vibration transducer. Oxy-hydro combustion pressure waves created at the active electrode during electrosurgery are detected and transformed into electrical signal outputs. These electrical signals can be comparatively analyzed against numerically regressed curves of oxy-hydro combustion signature acoustic intensity in control algorithms 130, as depicted in FIG. 2B. The acoustic sensor is electrically coupled to proportionality circuitry for providing both differential feedback 140 for electrosurgical console output parameters and integral feed-forward control 145 of adjunct devices that can provide additional inputs to the surgical field, such as irrigation systems and pumps similar to those disclosed in U.S. patent application Ser. No. 10/157,651. Additionally, piezo-acoustic sensor 390 can be used to detect Doppler sound shifts using time integration circuitry 120, as depicted in FIG. 2B, with information about known irrigation fluid density correlated from impedance control circuitry to perform basic densitometry, thereby detecting acid-base shifts due to the by-products of electrolysis induced by electrosurgical procedures. The densitometry/acoustic sensor is electrically coupled to proportionality circuitry 140 for providing both differential feedback for electrosurgical console output parameters and integral feed-forward control 145 of adjunct devices that can provide additional inputs to the surgical field, such as irrigation systems and pumps similar to those disclosed in U.S. patent application Ser. No. 10/157,651.

Figure 9:
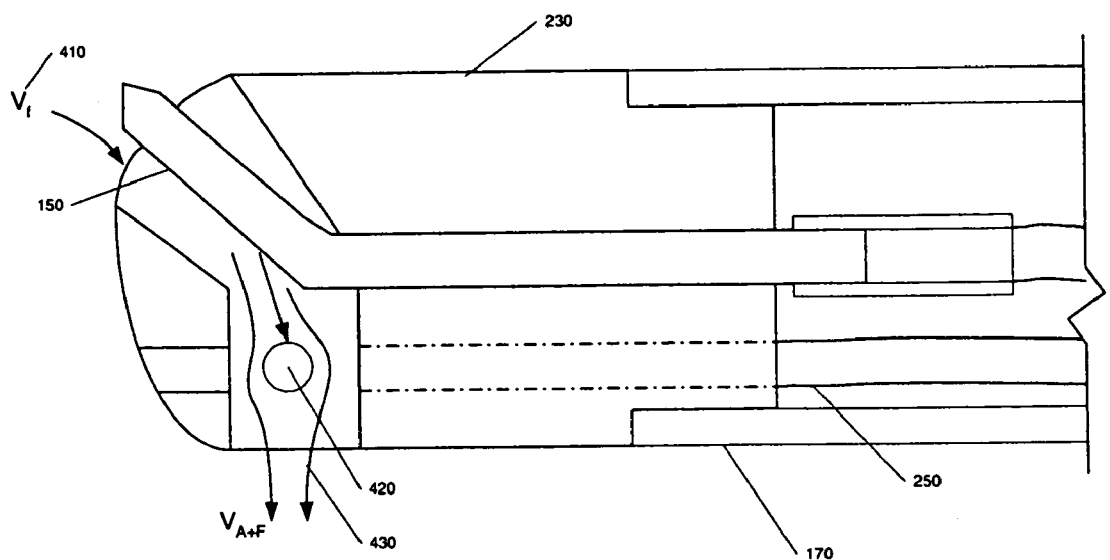
FIG. 9 is a view of a probe of the invention utilizing a single wire ion sensor.

FIG. 9 depicts yet another embodiment of an electrosurgical probe including a distal active electrode 159 and a proximal return electrode 170 separated by an insulator 230 wherein is disposed a pH-meter comprising a single wire ion meter 420 comprised of Mg—Ni or similar material connected to pH potential conductor wire 250 to detect acid-base shifts due to the byproducts of electrolysis induced by electrosurgical procedures. The pH sensor is optionally electrically coupled to proportionality circuitry 140 for providing both differential feedback for electrosurgical console output parameters and integral feed-forward 145 controls of adjunct devices that can provide additional inputs to the treatment field, such as irrigation systems and pumps similar to those disclosed in U.S. patent application Ser. No. 10/157,651.

Figure 10:
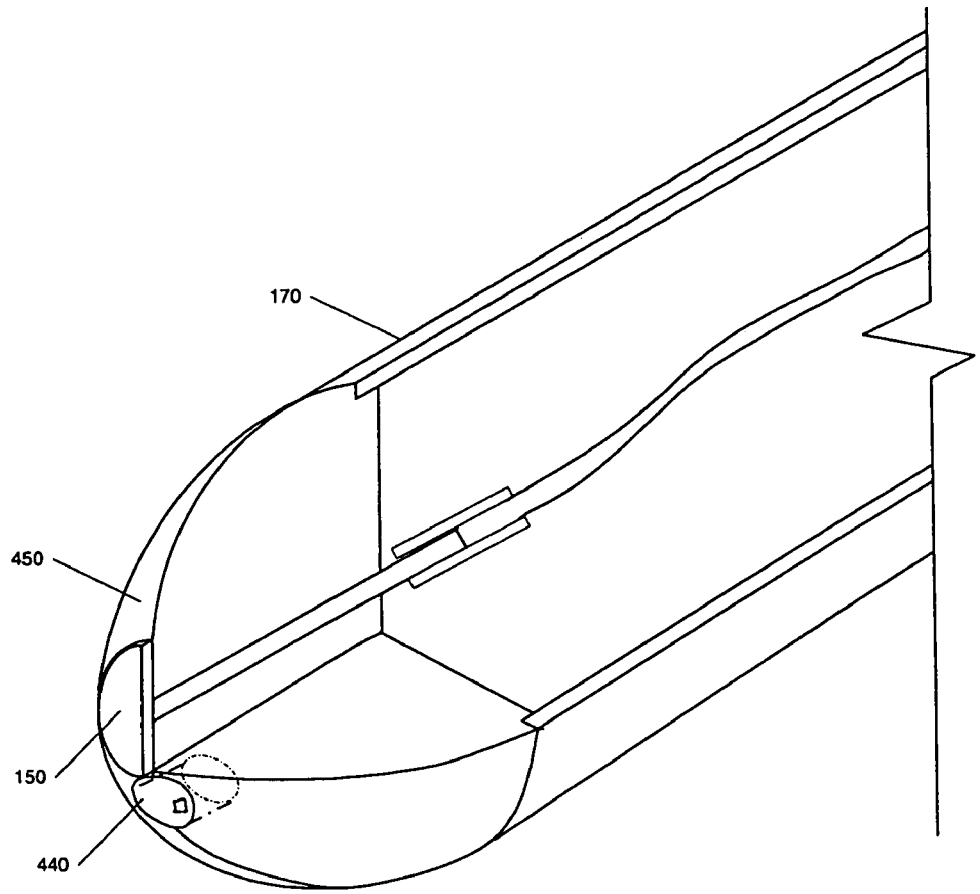
FIG. 10 is a view of a probe of the invention utilizing thermo-luminescent crystal material as an insert for a thermoluminescent crystal beacon.

FIG. 10 depicts yet another embodiment of an electrosurgical probe including an active electrode 150 and return electrode 170 separated by an insulating member 450 wherein is disposed at the distal tip a thermoluminescent crystal member 440 embedded in primary insulating member 450. The thermoluminescent crystal member acts as a "beacon" of localized temperature at the surgical site, providing means for visualization of real-time temperatures at the treatment site, additionally providing means to sense and display visual cues of temperature that are immune to interferences from propagating electromagnetic waves. The crystal element includes Europium-doped magnesium bromide crystalline structures. The crystalline structure is stabilized for the electrosurgical environment by means of an optically clear coating, such as a quartz silica glass or polymethylmethacrylate polymer. The thermo-luminescent crystal is disposed on the distal portion of the insulating member in proximity to active electrode 150. The energy flux between the active and return electrodes is the source of energy that drives electrolysis equations 10 and in so doing generates heat within the fluid surrounding the active electrode. The heat generated is both convectively and conductively transferred through the irrigant media and or tissue, depending upon treatment methods, and convectively and conductively heats insulating member 450 with thermo-luminescent element 440 disposed at the distal tip of the probe. As thermoluminescent element 440 is heated, molecular excitations cause electron orbital fluctuations and the release of photons of known wavelength. As the light and color shift of the crystal are correlated to its ambient temperature a direct visual aid is created that directly demonstrates the temperature of the energized probe. The clinician can then respond immediately to luminescence shifts in thermo-luminescent element 440 to appropriately meter probe activation and tissue treatment as well as power set points on the electrosurgical controller.

Figure 11:
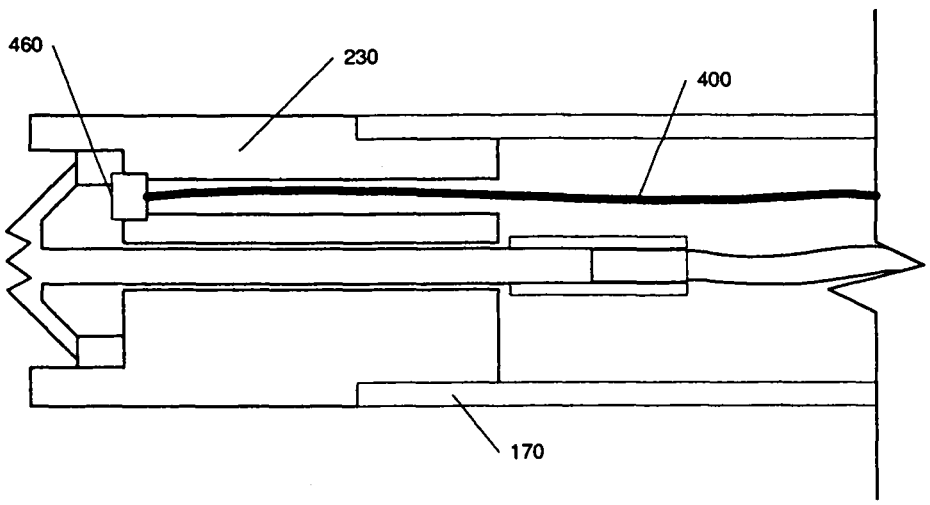
FIG. 11 is a view of a probe of the invention utilizing a thermoelectric semi-conductor as a piezo-electric pyrometer.

FIG. 11 depicts yet another embodiment of an electrosurgical probe wherein the sensor is pyrometric sensor 460 constructed of a thin-film thermal-electric compound, such as bismuth-telluride (available from the Hi-Z Corporation of San Diego, Calif.) connected to transducer conductor wire 400. This thermoelectric sensor is optionally electrically coupled to proportionality circuitry 140 for providing both differential feedback for electrosurgical console output parameters and integral feed-forward 145 controls of adjunct devices that can provide additional inputs to the treatment field, such as irrigation systems and pumps similar to those disclosed in U.S. patent application Ser. No. 10/157,651.

Figure 15:
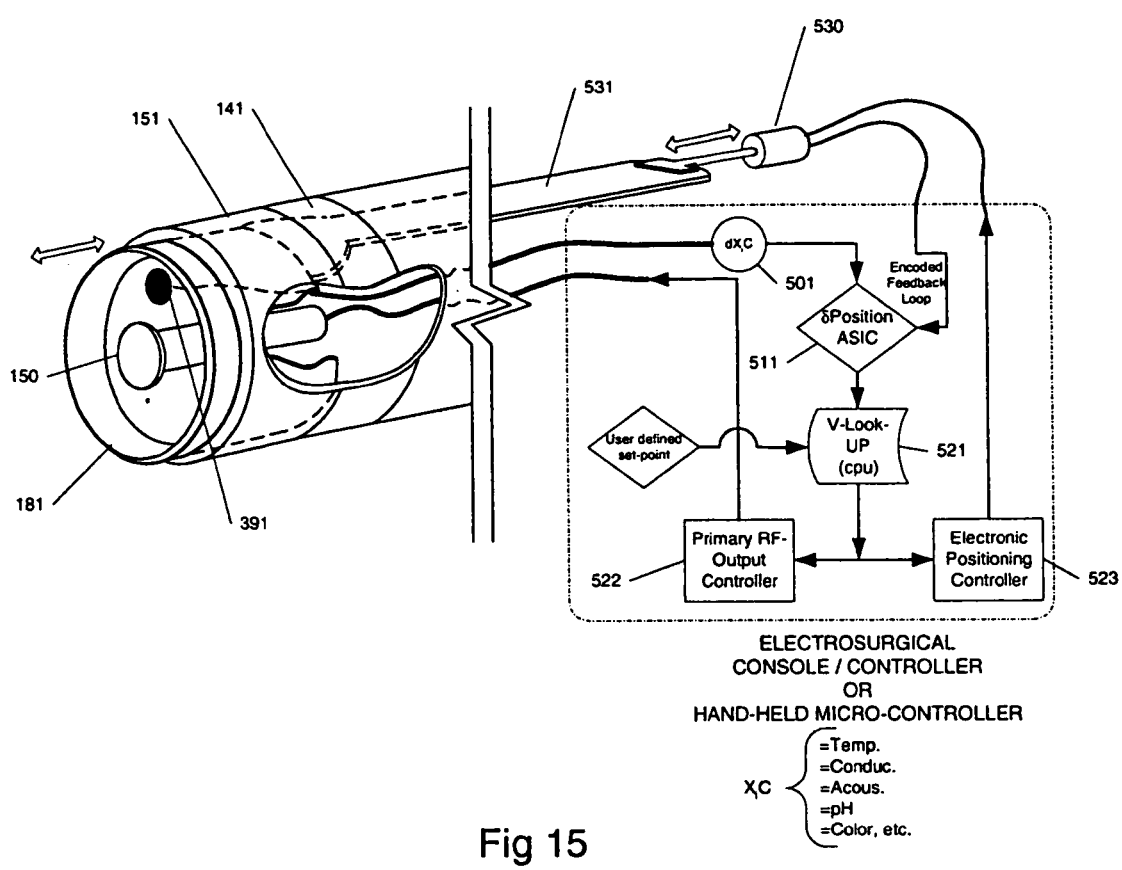
FIG. 15 is a view of a probe of the invention with an adjustable insulating cylindrical sleeve and at least one detector.

FIG. 15 depicts an embodiment of an electrosurgical probe which provides a means for maintaining the optimal spacing of active electrode 150, disposed distal from the primary lumen 141 which also acts as a return electrode. Actuating arm 531, which in turn is driven by electric positioning motor 530, actuates translatable sheath 181. Translatable sheath 181 thus can extend the insulating properties of insulator 151 beyond the end profile or position of active electrode 150, providing means to create a variable volume localized chamber when the translatable sheath 80 is extended. In an alternative embodiment, translatable sheath 181 can be mechanically actuated, including by means of a thumb control, which may incorporate gears or other means of transferring energy, utilized by the operator. Thus translatable sheath 181 may, in one embodiment, simply be frictionally engage with a thumb control or other means of movement, may be mechanically actuated, or may be electro-mechanically actuated, as in FIG. 15. In one embodiment, sensor 391 provides primary control variable feedback to differential controller 501, optionally as an analog input. If the input is analog, it may be output via flip-flop A/D conversion to a digital control signal for use by application-specific integrated circuitry logic controller 511, such as an FPGA, MOSFET, or similar intermediate digital logic gate controlling array. Flash RAM, and additional high level input/output governance, is controlled by CPU 521, utilizing software governed database lookup techniques, such as those commonly known in C+ or C++ programming code, to provide dual proportional output via Primary RF Output Controller/Generator 522; and further and optionally also to Electronic Positioning Controller 523 for simultaneous balanced positioning of translatable sheath 80 coupled to matched power setting through controller 522, providing the primary controlling input to match user set-points according to primary control variable known characteristics correlation to a desired set point. Electrical power may be provided by wires connected to a suitable source of power, which may be one or more sources of power, such as a high voltage source for operation of the active electrode and a lower voltage source for operation of the circuits provided. In the embodiment of FIG. 15, the detector or sensor employed may be any detector or sensor described herein.

It is further to be appreciated that a fixed cavity probe may be employed, such that one or more active electrodes are disposed within a cavity, the distal end of the probe ending beyond the end of the one or more active electrodes. Return electrodes may be provided, which return electrodes can be within the cavity or without the cavity, and in one embodiment are located on the exterior or interior surface of the probe on the portion of the probe forming a cavity. In this embodiment, one or more detectors or sensors may be provided, preferably located within the cavity. However, detectors or sensors may also be integrated into the probe body, such as by forming a part of the cavity wall, or may be located on the exterior of the probe.

Other detectors or sensors may be employed to determine parameters relevant to either electrolysis or to oxy-hydro combustion, or to both. In one embodiment, the detector detects local pressure changes, and includes a pressure sensor. Such pressure sensor may be employed to determine the position of a probe with respect to tissues, such as whether the probe touches a tissue, or may alternatively be employed to detect local pressure changes relating to either electrolysis or oxy-hydro combustion. In another embodiment, the detector detects consumption of interfacing media, particularly oxygen or hydrogen, such consumption including consumption by oxy-hydro combustion.

It is to be appreciated that the same sensor or detector may detect a parameter relating to electrolysis and also a parameter relating to oxy-hydro combustion, and may further detect parameters relating to the transition to oxy-hydro combustion. Thus electrolysis and oxy-hydro combustion may occur successively or simultaneously, and the relationship thereof can be monitored and determined by means of data collected by the sensor or detector.

It is also to be appreciated that any of the probes or devices disclosed herein may have two or more active electrodes, and may also have two or more return electrodes. In some embodiments, the return electrode may form a part of the body of the probe. Similarly, two or more different detectors or sensors may be provided, determining two or more different parameters. Alternative, two or more detectors or sensors may be provided, but at different locations on the probe, providing relevant information about either electrolysis or oxy-hydro combustion. For example, one temperature probe may be located at the distal end of the probe, to measure temperature at the site closest to tissue being treated, while a second temperature probe may be removed some distance, such as by locating on an insulated exterior surface of the probe, to determine the area of temperature change. Other such combinations and permutations are both possible and contemplated.

FIG. 1A illustrates a preferred embodiment of the physiochemistry of the electrolysis and oxy-hydro combustion reaction. The physiochemistry of the electrosurgical process consists of an acid-base shift that governs the relative availability amount of water that can be consumed as part of an electrolysis chemical reaction. The electrolysis reaction is driven by the high energy density/flux modes of operation of electrosurgical probes. FIG. 1A illustrates the chemical equation that describes the overall electrolysis and oxy-hydro reaction as it pertains to electrosurgery in the underwater, cellular, and biologic environment. From this reaction it is noted that all the necessary chemical participants are accounted for and that the physical observations of light emission and heat generation are also accounted for. The series of chemical equations 10 that govern the process first provide an electrolysis function thereby liberating elemental oxygen and hydrogen gas 30. Given that the entire electrosurgical process is typically observed to occur fully immersed in a saline solution (0.9% by weight) the presence of sodium chloride (NaCl) must also be accounted for. The normal stoichiometry of the electrolysis reaction dictates that when elemental gas separation is occurring, then the solute participants must join with the remaining solution components of water to form a complementary acid-base pair. This pair is clearly shown on the right-hand side of the upper half of equations 10 as a hydrochloric acid 15 and sodium hydroxide 20 base pair. The hydrogen and oxygen gases 30 can be co-mingled without immediate spontaneous exothermic reaction. A small amount of energy, such as the radio frequency energy 40 indicated in the lower of equations 10, needs to be added to overcome the nominally endothermic reaction and ignite the oxy-hydro combustion. Once ignited, the reaction will cascade, or self-perpetuate, until all the reactants are consumed and reduced to the products shown on the right-hand side of the lower equations 10.

FIG. 1B illustrates a variation of the acid-base throttling reaction of the preferred embodiment. It is worthy of note that the entire electrolysis and oxy-hydro combustion process is a dynamic process, occurring in a fixed reservoir of fluid, which necessarily implies dynamically changing concentrations of salt ions, based on water volume converted to elemental gas. This suggests that as the acid-base shift occurs in the reservoir less and less water is available for electrolysis. This reaction is clearly seen in FIG. 1B where the acid-base pair 15 and 20 is shown in increased molar proportion to the normal stoichiometric quantity of the base reactions 10. The reduction of available water for electrolysis is evident in relationship 50 of oxygen and hydrogen gas to acid-base pair. The explanation for this is evident from the stoichiometry—insufficient water is available, given the fixed eight (8) moles of water to start with a finite reservoir of water, and the increasing molar concentration of acid and base as the oxygen and hydrogen are liberated away from the solution in the gas state, such as by bubbling out of solution. It is illustrated as fewer moles of the oxy-hydrogen gas present after electrolysis in FIG. 1B, wherein the balancing portion of the atoms account for the dynamic increase acid-base concentration.

FIG. 1C illustrates the more general case of the electrolysis and oxy-hydro combustion reaction process wherein the ionic salt is represented by variable 60, X which could be any of the appropriate group I, period 1-7 elements of the periodic table. This generalized reaction case shows how the hydronium and hydroxide ions can contribute to the same overall chemical reaction known as electrolysis and oxy-hydro combustion.

FIG. 1D illustrates the more general case of the electrolysis and oxy-hydro combustion reaction process wherein the ionic salt is represented by variables 61, $\alpha$, $\beta$, $\gamma$, $\delta$, the molar quantities required for stoichiometric combustion could be any value that appropriately satisfies the oxidation reduction valence requirements for the overall reaction. This generalized reaction case shows how the oxygen and hydrogen requirements can vary and still result in the same overall chemical reaction known as electrolysis and oxy-hydro combustion.

Understanding of the foregoing reaction conditions makes clear the utility of sensors or detectors proximal to the active electrode for local measurement of relevant parameters, such as temperature, pH, conductivity, impedance, ion concentrations, gas production—particularly hydrogen or oxygen production, and sound. Determination of relevant parameters allows adjustment in operation of the electrolysis probe, such as adjusting power, radiofrequency, electrolytic media flow or composition, and the like.

FIG. 2A and FIG. 2B illustrate both general and specific cases of control mechanisms by which relevant parameters of electrosurgical process can be accurately governed. Ordinary signal transduction from the instrumentation corporeal contact part to the electrosurgical controller is required to provide means for input signal recording using time integration circuitry 110 and performing subsequent mathematical operations 120 to condition the input signal so as to use it effectively as a stable control variable. For example, analog detector signals acquired from any of the probes of FIG. 3, 4, 6, 7A, 7B, 8, 9, 10 or 11 can be converted by analog-to-digital converter 100. After recording using time integration circuit 110 mathematical operations 120, such as microprocessor driven software algorithms, may be employed, optimally using software algorithms 130 for comparison of time-averaged data points against a determined data standard. Such mathematical algorithms can include averaging, integration, differential rate of change calculations, and the like. In a specific case, a simple time averaging algorithm 70 of specified periodicity can be applied to the data stream to "smooth" the feedback signal and provide general control based on real-time trend information of selected parameters. Such control output can be performed in the manner of ratio controlling 90 and 140 to "throttle" equipment output functions based on sensed/detected parameters at the surgical site. Standard communications links 145 can be used to interconnect adjunct equipment to the electrosurgical controller or other ratio-controller that works in tandem with the electrosurgical controller.

FIG. 3 illustrates use of encapsulated thermoluminescent crystal 160 to perform real-time visual feedback to the practitioner of temperature shifts at the treatment site. When active electrode 150 is energized and conducts high frequency electrical current to return electrode 170 the normal process of electrolysis of aqueous media 166 immediately begins. The endothermic reaction requires the input of energy that subsequently heats the aqueous media, convectively and conductively heating thermoluminescent crystal 160. As the thermoluminescent crystal emissions rise proportionally with temperature rise the luminance is captured by optical fiber ball end lens 180 and transmitted down optical fiber 190 to an opto-electrical coupling within an electrosurgical controller unit. The opto-electrically transformed signal thus provides means for input signal recording using time integration circuitry 110 and performing subsequent mathematical operations 120 to condition the input signal so as to use it effectively as a stable control variable. The mathematical algorithms can include averaging, integration, differential rate of change calculations, and the like. In this specific case, a colorimetric averaging algorithm 120 can be employed from known color correlating data to crystal dynamics to "quantize" the feedback signal and provide general control based on real-time trend information of selected parameters. Such control output can be performed in the manner of ratio controlling 140 to "throttle" equipment output functions based on sensed/detected parameters at the treatment site. Standard communications links 145 can be used to interconnect adjunct equipment to the electrosurgical controller or other ratio-controller that works in tandem with the electrosurgical controller.

FIG. 4 illustrates use of pH sensing within the electrode-insulator combination to provide a stable control variable for governing electrosurgical process. In this embodiment, miniature glass bulb pH sensor 240 is disposed within a semi-enclosed cavity of the electrode insulator combination 230 and 150. Acid-base shifted water can accumulate within the cavity and flow out of acid-water outflow portal 220. As the rate of electrolysis and oxy-hydro combustion increases or decreases production of acid-base pairs also increases or decreases, and thus there are changes in pH of the immediate space surrounding active electrode 150. The pH signal is transduced along conductor wire 250, optionally to an analog to digital flip-flop circuit where the signal is transformed for use in software algorithms as a stable control variable. Such mathematical algorithms can include averaging, integration, differential rate of change calculations, and the like. In this specific case, a logarithmic averaging algorithm 120 from acid-base shift rates of change data correlated to electrolysis and oxy-hydro combustion rates is employed to "quantize" the feedback signal and provide general control based on real-time trend information of selected parameters. Such control output can be performed in the manner of ratio controlling 140 to "throttle" equipment output functions based on sensed/detected parameters at the treatment site. Standard communications links 145 can be used to interconnect adjunct equipment to the electrosurgical controller or other ratio-controller that works in tandem with the electrosurgical controller.

FIG. 6 depicts use of optical fiber sensing at and within the distal tip of a probe as part of an array of independently connected optical fibers providing means to sense both internal and external to the distal tip of the electrosurgical probe. Internal optical fiber 195 uses ball ended lens 340 to collect light emitted from within the insulating member, such as a thermoluminescent crystal or europium doped yttria-stabilized-zirconia crystal 230. External optical fiber 190 uses a ball ended lens 345 to collect infrared light emitted from the surgical site, with ball ended lens 345 being comprised of a spherical lens with a ground-in focal point of approximately 3-5 mm. The optical fiber is optionally made of a single-mode silica glass optimized for the transmission of infrared light, well known to those skilled in the art of optical fiber production. In an additional control algorithm, alternative ball end lens 345 can be optically switched at the controller unit to an alternative detector designed to measure gas production using gas filter correlation radiometry or Fourier infra-red spectroscopy. In this specific case, spectral averaging algorithm 120 from electrolysis and oxy-hydrogen gas production rate data is correlated to thermal rise created by nominal electrolysis and oxy-hydro combustion heat of reaction to "quantize" the feedback signal and provide general control based on real-time trend information of selected parameters. Such control output can be performed in the manner of ratio controlling 140 to "throttle" equipment output functions based on sensed/detected parameters at the treatment site. Standard communications links 145 can be used to interconnect adjunct equipment to the electrosurgical controller or other ratio-controller that works in tandem with the electrosurgical controller.

FIG. 7A and FIG. 7B depict use of conductivity electrode pair 350 and 360 separated by insulating member 230 to sense the changes in conductivity that electrolysis induces through the creation of acid-base pairs. Electrolysis occurs when active electrode 150 is electrically energized and conducts current to return electrode 170, forming acid-base pairs which alter the natural conductivity of traditionally utilized electrosurgical irrigants. As the resulting hydronium ion concentrations are raised and lowered the conductivity of the surrounding fluid is also raised and lowered. The generally accepted methodology for detecting conductivity is the application of a known DC voltage across electrode pairs 350 and 360 while measuring the current flow through the conductive media. Electrical conductors 370 and 380 carry the current through a detection loop circuit within the electrosurgical controller. In one instance, time averaging algorithm 70 from acid-base pair conductivity shift data is correlated to pH change which in turn can be correlated to treatment response catalog data to "quantize" the feedback signal and provide general control based on real-time trend information of selected parameters. Controlling acid-base pair production along treatment response constraints allows for improved overall treatment response and reduced collateral damage. Such control output can be performed in the manner of ratio controlling 140 to "throttle" equipment output functions based on sensed/detected parameters at the treatment site. Standard communications links 145 can be used to interconnect adjunct equipment to the electrosurgical controller or other ratio-controller that works in tandem with the electrosurgical controller.

FIG. 8 depicts use of a piezo-electric acoustic sensor to transmit sound waves generated by oxy-hydro combustion from the electrode-insulator interface to the electrosurgical controller. Piezo-acoustic sensor 390 is tuned to operate in the 10 kHz to 600 kHz range of sound output. From the probe specific response data, characteristic sound thresholds are established that allow the conducted analog acoustic signal carried in transducer conductor wire 400 to be converted via A/D flip-flop for use in software comparative algorithms 140. Each quantized acoustic increment can be accurately correlated to oxy-hydro combustion rates. As active electrode 150 is energized and completes the circuit with return electrode 170 the normal electrolysis phenomenon occurs. The sound levels associated with this tend to be very low, as only a small number of cavitations of formed bubbles are present. As the power delivered via active conductor 200 is steadily increased, the rate of gas formation increases, along with the rate of bubble collapse. Sound levels steadily increase until specific stoichiometric combinations of oxygen and hydrogen gases have been achieved and the oxy-hydro combustion chain reaction is initiated. As the rate of oxy-hydro combustion is further increased, the combustion volume increases, as does its sound output. A time sequence comparison of the sampled data can be run to determine trend data for establishing a stable control variable. Such control output can be performed in the manner of ratio controlling 140 to "throttle" equipment output functions based on sensed/detected parameters at the treatment site. Standard communications links 145 can be used to interconnect adjunct equipment to the electrosurgical controller or other ratio-controller that works in tandem with the electrosurgical controller.

FIG. 9 depicts use of the alternative pH-sensing embodiment utilizing single wire ion-specific detector 420, which is accurately correlated to probe power output and acid-base shift at the treatment site and circuitry for governing electrosurgical processes. The ion specific pH wire sensor is, in one embodiment, made of an Mg—Ni metal alloy for sensing capacitive shift in the presence of $Cl^-$ ions or similar metal alloy for sensing $Na^+$ ions. As active electrode 150 is energized and current flows to return electrode 170 the fundamental electrolysis reactions 10 take place, producing acid-base shifts in the media or material immediately about the active electrode. Irrigation fluid electrolyte 410 is drawn toward the active electrode as part of the convective forces induced by normal heating of the active electrode 150. Flow is further induced by suction flow of acid-base pairs of higher density 430 flowing away from the active electrode due to gravitational acceleration and convective forces. The conductor wire for the pH ion detector wire 250 delivers the capacitive shift data driven by the presence of acid-base pairs at the sensor 420. This capacitive shift can be converted at the electrosurgical controller to a digital signal via A/D flip-flop for use in software driven algorithms.

FIG. 10 depicts use of thermo-luminescent crystal beacon element 440 to provide visual feedback system to the practitioner for understanding treatment site temperature. The crystal element includes europium doped magnesium bromide crystalline structures. The crystalline structure is optionally stabilized for the electrosurgical environment, such as by means of an optically clear coating, for example a quartz silica glass or polymethylmethacrylate polymer. The thermoluminescent crystal is disposed on the distal portion of the insulating member in proximity of the active electrode 150. Proximity to active electrode 150 provides means to sense both contact conducted temperature of the actual treatment site being affected by the energy flux completing the circuit between active electrode 150 and return electrode 170. This energy flux is the source of energy that drives electrolysis equations 10 and, in so doing, generates heat within the fluid surrounding the active electrode. The heat generated is both convectively and conductively transferred through the irrigant media, and convectively and conductively heats insulating member 450 with thermo-luminescent element 440 disposed at the distal tip of the probe. As the thermo-luminescent element 440 is heated, molecular excitations cause electron orbital fluctuations and the release of photons of known wavelength. As the light and color shift of the crystal are correlated to its ambient temperature a direct visual aid is created that directly illustrates the temperature of the energized probe. The practitioner can then respond immediately to luminescence shifts in thermo-luminescent element 440 to appropriately meter probe activation and treatment as well as power set points on the electrosurgical controller.

FIG. 11 depicts use of thermoelectric semi-conductor 460 constructed of bismuth-telluride. As the active electrode is activated, electrolysis is initiated and dependent on total power input rates increase to the ignition point of sustained oxy-hydro combustion. As the total power input is increased, localized heating of the conductive intermediary agent, irrigant, or media is raised. The thermoelectric sensor develops intermolecular excitations from the increase in temperature and subsequently conducts current at the electrons in the semi-conductor translate, a technique familiar to those skilled in the art of Pelltier type thermoelectric generators. The thermoelectrically generated current is conducted along conductor 400 and is coupled to the electrosurgical controller and can be used as disclosed above to perform both basic and advanced control functions based on localized treatment site temperature. As should become evident to those skilled in the art, the thermoelectric sensor can easily be substituted with a piezo-electric thin-film pyrometer that functions in a similar manner to the bismuth-telluride semiconducting thermoelectric materials.

Figure 12:
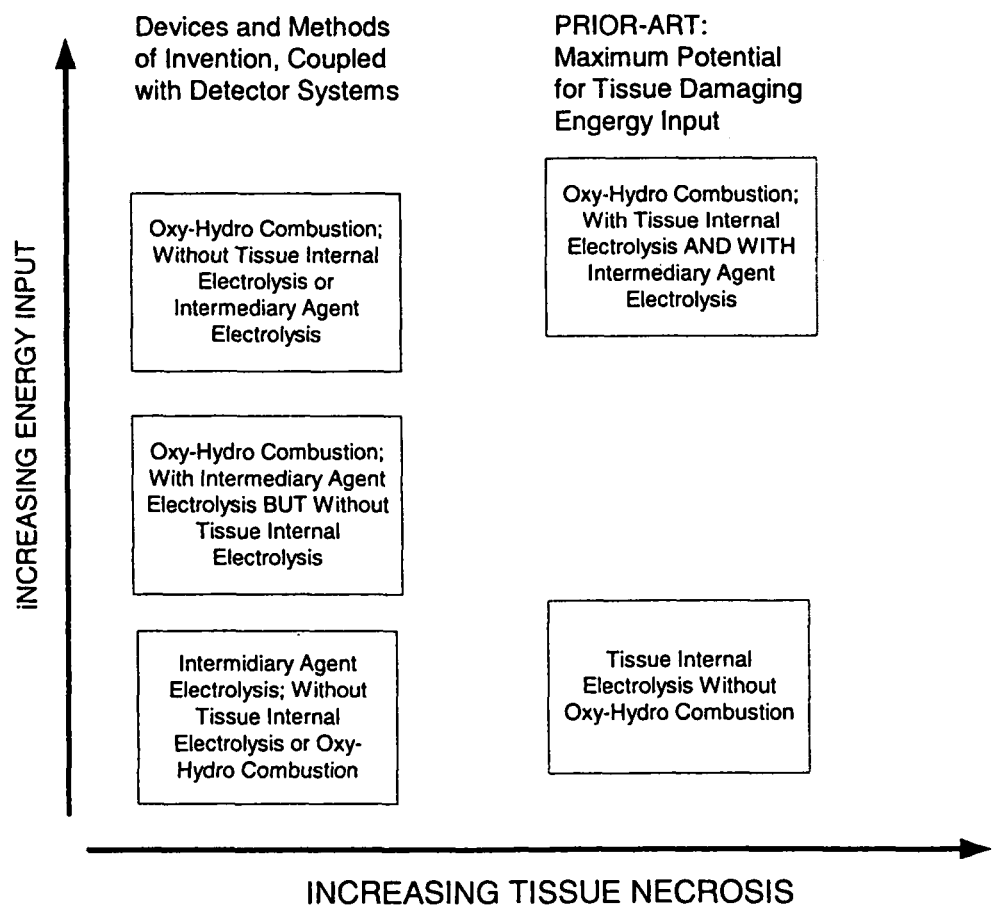
FIG. 12 is an electrosurgical map which provides the arenas in which the methods and devices disclosed herein may be utilized.

Accordingly, the use of methods and devices that allow sensing, detecting, measuring, and controlling relevant parameters of electrosurgery as described in this invention provide for new and unexpected advantages to the medical practitioner and patient in improving electrosurgical treatments, providing better control of electrosurgical treatments, and improving overall efficaciousness of electrosurgical treatments, as depicted in FIG. 12. This occurs due to improved understanding of physiochemical interactions which are accurately controlled for such outcomes. For example, these sensing, measuring, and detecting methods and devices for electrosurgery allow for the accurate therapeutic use of the electrolysis and oxy-hydro combustion reactions during electrosurgery. This allows the practitioner to harness the electrolysis and/or the oxy-hydro combustion portions of the electrosurgical phenomenon designed for specific therapeutic interventions by sensing, measuring, and detecting relevant parameters of electrosurgery. In one instance, for those procedures which rely upon the electrolysis portion of the electrosurgical phenomenon alone, the determination of when oxy-hydro combustion is occurring is important so that oxy-hydro combustion can be avoided in those settings. In another instance, for those procedures which rely upon the oxy-hydro combustion portion of the electrosurgical phenomenon alone, the determination of when electrolysis is occurring is important so that electrolysis can be avoided in those settings. In yet another instance, for those procedures which rely upon both the electrolysis and the oxy-hydro combustion portion of the electrosurgical phenomenon, the determination of when each reaction is occurring is important so they can be regulated in those settings. These determinations can be via sensing, measuring, or detecting temperature, pH, gas production, conductivity, ions, acoustic parameters, and the like at the electrosurgical treatment site, which optionally are translated to visible or controller indication/feedback of the actual probe system and treatment site occurrences. This enables the devices and instrumentation to self-regulate as to when it is appropriate to decrease or increase energy input or other local parameters, such as irrigants, temperature, acid-base flush, salt concentration, and the like, so that the reactions can be more accurately controlled. Further, the practitioner will have additional information regarding the specific treatment locale so that yet another level of control can be imposed upon the treatment venue.

Those skilled in the art will clearly see that controls for modern electrosurgery should rely upon sensing electrosurgical physiochemistry to better inform practitioners of potential harmful effects of electrosurgical treatments that are not desired for a particular therapeutic application. Furthermore, these methods and devices provide knowledge of the actual mechanisms at work in electrosurgery procedures that provide new paradigms for treatments heretofore unrecognized, to thereby enhance surgical outcomes.

The scope of the invention should be determined by the appended claims and their legal equivalents, rather than by the examples given. The preceding examples can be repeated with similar success by substituting the generically or specifically described elements and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An apparatus for electrosurgery, comprising:
   at least one active electrode for inducing electrolysis in an electrolyzable environment at a distal end of the apparatus; and
   at least one detector proximal to the at least one active electrode for detecting a-temperature at the surgical site,
   wherein the at least one detector comprises a thermo-luminescent crystal or a piezo-electric pyrometer adjacent to the at least one active electrode at the distal end of the apparatus that provides to a user a visible indication of the temperature at the surgical site at the at least one detector and wherein the at least one detector is positioned within the surgical site when the apparatus is in use.

2. The apparatus of claim 1, wherein the piezo-electric pyrometer comprises a thin-film piezo-electric pyrometer.

3. The apparatus of claim 1, further comprising a return electrode.

4. The apparatus of claim 1, further comprising a detection circuit for receiving a parameter detected by the detector.

5. The apparatus of claim 1, wherein there is one active electrode.

6. The apparatus of claim 1, further comprising a probe body with a distal end and a proximal end, with at least one active electrode disposed on the distal end.

7. The apparatus of claim 1 further comprising an electrosurgical controller that incorporates a temperature signal generated by the thermo-luminescent crystal in control algorithms to meter power output to the active electrode.

* * * * *